(12) United States Patent
Burger et al.

(10) Patent No.: US 8,759,338 B2
(45) Date of Patent: Jun. 24, 2014

(54) HETEROCYCLIC KINASE INHIBITORS

(75) Inventors: Matthew Burger, Emeryville, CA (US); Jiong Lan, Emeryville, CA (US)

(73) Assignee: Novartis AG, Basel (CH)

( * ) Notice: Subject to any disclaimer, the term of this patent is extended or adjusted under 35 U.S.C. 154(b) by 359 days.

(21) Appl. No.: 13/061,009

(22) PCT Filed: Aug. 31, 2009

(86) PCT No.: PCT/EP2009/061188
§ 371 (c)(1),
(2), (4) Date: Apr. 27, 2011

(87) PCT Pub. No.: WO2010/026122
PCT Pub. Date: Mar. 11, 2010

(65) Prior Publication Data
US 2011/0195956 A1  Aug. 11, 2011

Related U.S. Application Data

(60) Provisional application No. 61/093,664, filed on Sep. 2, 2008.

(51) Int. Cl.
*A61K 31/55* (2006.01)
*A61K 31/517* (2006.01)
*C07D 403/00* (2006.01)
*C07D 401/00* (2006.01)

(52) U.S. Cl.
USPC ............ 514/217.06; 514/266.21; 514/266.22; 540/600; 544/284

(58) Field of Classification Search
None
See application file for complete search history.

(56) References Cited

U.S. PATENT DOCUMENTS

2007/0287708 A1  12/2007  Cole et al.

FOREIGN PATENT DOCUMENTS

| WO | WO 95/00511 | 1/1995 |
|---|---|---|
| WO | WO 00/12497 | 3/2000 |
| WO | WO 2004/046133 | 6/2004 |
| WO | WO 2004/081000 | 9/2004 |
| WO | WO 2004/108707 | 12/2004 |
| WO | WO 2005033105 A2 * | 4/2005 |
| WO | WO 2007/027729 | 3/2007 |
| WO | WO 2007/076092 | 7/2007 |
| WO | WO 2007/146376 | 12/2007 |
| WO | WO 2008/028168 | 3/2008 |

OTHER PUBLICATIONS

Bremer et al., "The Significance of the Graeb-Ulmann Carbazole Synthesis and its Application to N-Substituted Pyridinotriazoles" *Justus Liebigs Annalen Der Chemie 514*:279-291, 1934.
Morley et al. "The Chemistry of Simple Heterocyclic Systems. Part II Condensations of 4-Chloro-6- and 4-Chloro-7-nitroquinazoline with Amines" Journal of the Chemical Society pp. 1014-1017, Jan. 1, 1949.

* cited by examiner

*Primary Examiner* — Emily Bernhardt
*Assistant Examiner* — Oluwafemi Masha
(74) *Attorney, Agent, or Firm* — Michael G. Smith

(57) ABSTRACT

New compounds, compositions and methods of inhibition of Provirus Integration of Maloney Kinase (PIM kinase) activity associated with tumorigenesis in a human or animal subject are provided. In certain embodiments, the compounds and compositions are effective to inhibit the activity of at least one PIM kinase. The new compounds and compositions may be used either alone or in combination with at least one additional agent for the treatment of a serine/threonine kinase- or receptor tyrosine kinase-mediated disorder, such as cancer.

10 Claims, No Drawings

HETEROCYCLIC KINASE INHIBITORS

CROSS-REFERENCE TO RELATED APPLICATION

This application is a U.S. National Phase filing of International Application No. PCT/EP2009/061188 filed Aug. 31, 2009, and claims the benefit under 35 U.S.C. §119(e) to U.S. provisional application Ser. No. 61/093,664, filed on Sep. 2, 2008, which is incorporated herein in its entirety by reference.

FIELD OF THE INVENTION

The present invention relates to new compounds and their tautomers and stereoisomers, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Infection with the Maloney retrovirus and genome integration in the host cell genome results in development of lymphomas in mice. Provirus Integration of Maloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," *Cell* 37(1): 141-50 (1984); Selten G, et al., "Proviral activation of the putative oncogene Pim-1 in MuLV induced T-cell lymphomas" *EMBO J* 4(7):1793-8 (1985)), thus establishing a correlation between over-expression of this kinase and its oncogenic potential. Sequence homology analysis demonstrated that there are 3 highly homologous Pim-Kinases (Pim1, 2 & 3), Pim1 being the proto-oncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" *Nature* 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" *Mol Cell Biol* 11(2):1176-9 (1991)). Thus, these animal models establish a strong correlation between Pim over-expression and oncogenesis in hematopoietic malignancies. In addition to these animal models, Pim over-expression has been reported in many other human malignancies. Pim1, 2 & 3 over-expression is frequently observed in many hematopoietic malignancies (Amson R et al., "The human protooncogene product p33pim is expressed during fetal hematopoiesis and in diverse leukemias," *PNAS USA* 86(22):8857-61 (1989); Cohen A M et al., "Increased expression of the hPim-2 gene in human chronic lymphocytic leukemia and non-Hodgkin lymphoma," *Leuk Lymph* 45(5):951-5 (2004), Huttmann A et al., "Gene expression signatures separate B-cell chronic lymphocytic leukaemia prognostic subgroups defined by ZAP-70 and CD38 expression status," *Leukemia* 20:1774-1782 (2006)) and in prostate cancer (Dhanasekaran S M, et al., "Delineation of prognostic biomarkers in prostate cancer," *Nature* 412(6849): 822-6 (2001); Cibull T L, et al., "Overexpression of Pim-1 during progression of prostatic adenocarcinoma," *J Clin Pathol* 59(3):285-8 (2006)), while over-expression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," *Int J Cancer* 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," *Cancer Res* 66(13):6741-7 (2006)).

Pim1, 2 & 3 are Serine/Threonine kinases that normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling down stream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Ser112 gatekeeper site: *FEBS Letters* 571: 43-49 (2004)), cell cycle regulators such as $p21^{WFA1/CIP1}$ (Wang Z, et al., "Phosphorylation of the cell cycle inhibitor p21Cip1/WAF1 by Pim-1 kinase," *Biochim Biophys Acta* 1593:45-55 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," *J Biol Chem* 179:48319-48328 (2004)) and NuMA (Bhattacharya N, et al., "Pim-1 associates with protein complexes necessary for mitosis," *Chromosoma* 111(2): 80-95 (2002)) and the protein synthesis regulator 4EBP1 (Hammerman P S et al., "Pim and Akt oncogenes are independent regulators of hematopoietic cell growth and survival," *Blood* 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers on which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," *Acta Pharmacol Sin* 26(3):364-8 (2005); Fujii et al. 2005; Li et al. 2006). Furthermore, mutational activation of several well know oncogenes in hematopoietic malignancies are thought exert its effects at least in part through Pim(s). For example, targeted down regulation of pim expression impairs survival of hematopoietic cells transformed by Flt3 and BCR/ABL (Adam et al. 2006). Thus, inhibitors to Pim1, 2 &3 would be useful in the treatment of these malignancies. In addition to a potential role in cancer treatment and myeloproliferative diseases, such inhibitor could be useful to control expansion of immune cells in other pathologic condition such as autoimmune diseases, allergic reactions and in organ transplantation rejection syndromes. This notion is supported by the findings that differentiation of Th1 Helper T-cells by IL-12 and IFN-$\alpha$, results in induction of expression of both Pim1 & 2 (Aho T et al., "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al. 2005). These results suggest that Pim kinases are involved in the early differentiation process of Helper T-cells, which coordinate the immunological responses in autoimmune diseases, allergic reaction and tissue transplant rejection.

A continuing need exists for compounds that inhibit the proliferation of capillaries, inhibit the growth of tumors, treat cancer, modulate cell cycle arrest, and/or inhibit molecules such as Pim1, Pim2 and Pim3, and pharmaceutical formulations and medicaments that contain such compounds. A need also exists for methods of administering such compounds, pharmaceutical formulations, and medicaments to patients or subjects in need thereof.

SUMMARY

The present invention provides compounds of Formula I:

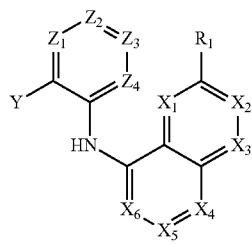

I their stereoisomers, tautomers, and pharmaceutically acceptable salts thereof, wherein:

$X_1$, $X_2$, $X_3$, $X_4$, $X_5$, and $X_6$ are independently selected from $CR_2$ and N, provided that at least one and not more than three of $X_1$, $X_2$, $X_3$, $X_4$, $X_5$, and $X_6$ are N;

Y is selected from a group consisting of amino, alkoxy, aryl, heteroaryl, partially unsaturated cycloalkyl, cycloalkyl, and heterocycloalkyl, wherein each member of said group is substituted with up to four substituents;

$Z_1$, $Z_2$, $Z_3$, and $Z_4$ are independently selected from $CR_{12}$ and N; provided that not more than two of $Z_1$, $Z_2$, $Z_3$, and $Z_4$ are N;

$R_1$ selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cyclo alkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

In some embodiments, compounds of Formula I, or a stereoisomer, tautomer, or pharmaceutically acceptable salt thereof, are provided wherein $X_1$ is N, $X_2$ and $X_6$ are $CR_2$ or N, and $X_3$, $X_4$, and $X_5$ are $CR_2$. In other embodiments, compounds of Formula I are provided wherein $Z_3$ is N, and one of, $Z_1$, $Z_2$, and $Z_4$ are selected from $CR_{12}$ and N, provided that no more than one of $Z_1$, $Z_2$, and $Z_4$ are N. In some embodiments, compounds of Formula I are provided wherein $X_2$ is N, and $X_6$ is $CR_2$. In yet other embodiments, new compounds of Formula I are provided wherein $Z_3$ is N, and $Z_1$, $Z_2$, and $Z_4$ are $CR_{12}$.

Another embodiment provides compounds of Formula II:

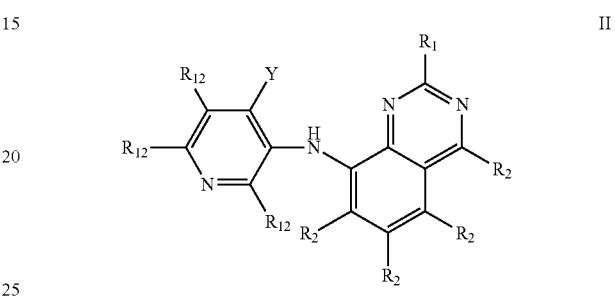

II or a stereoisomer, tautomer, or pharmaceutically acceptable salt thereof, wherein Y is selected from a group consisting of partially unsaturated cycloalkyl, cycloalkyl, and heterocycloalkyl, wherein each of member of said group is substituted with up to 4 substituents selected from halo, alkyl, hydroxyalkyl, haloalkyl, amino, substituted amino, hydroxyl, alkoxy, aryl, heteroaryl and cyano; and $R_1$ is selected from a group consisting of aryl, heteroaryl, alkyl, cycloalkyl, heterocycloalkyl, wherein each member of said group is substituted with up to 4 substituents selected from hydrogen, halogen, alkyl, alkenyl, alkynyl, amino, hydroxyl, alkoxy, carboxamido, sulfonyl and cyano; and $R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

In other embodiments are provided compounds of Formula I or II, or a stereoisomer, tautomer, or pharmaceutically acceptable salt thereof, wherein $R_2$ and $R_{12}$ are independently selected from hydrogen, halo, hydroxyl, amino, cyano, $C_{1-4}$ alkoxy and $C_{1-4}$ alkyl.

Yet other embodiment provides compounds of Formula I or II, or a stereoisomer, tautomer, or pharmaceutically acceptable salt thereof, wherein Y is selected from a group consisting of heterocycloalkyl, partially unsaturated cycloalkyl and cycloalkyl, wherein each member of said group is substituted with up to 4 substituents selected from hydrogen, halo, hydroxyl, nitro, cyano, $SO_3H$, substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, heterocycloalkyl, partially saturated cycloalkyl, aryloxy, heteroaryloxy, heterocyclyloxy, cycloalkyloxy, acyl, acylamino and acyloxy, and partially saturated cycloalkyl. In other embodiments, compounds of Formulas I or II are provided wherein Y is selected from a group consisting of piperidinyl, cycloalkyl, partially unsaturated cycloalkyl, piperazinyl, pyrrolidinyl, and azepan, wherein each member of said group is substituted with up to 4 substituents selected from hydrogen, halo, haloalkyl, hydroxyl, cyano, and substituted or unsubstituted alkyl, alkenyl, alkynyl, alkoxy, amino, cycloalkyl, hetero cycloalkyl, aminocarbonyloxy, amino sulfonyl, hydroxyalkyl, aminosulfonyloxy, amino sulfonylamino, amidino, carboxyl, carboxyl ester, (carboxyl ester) amino, aryl, heteroaryl, aryloxy, heteroaryloxy, heterocyclyloxy, cycloalkyloxy, acyl, acylamino and acyloxy. In yet other embodiments, compounds of Formulas I or II are provided Y is selected from a group consisting of piperidinyl, cyclohexyl, partially unsaturated cyclohexyl, azepane, pyrrolidinyl, and piperazinyl, wherein each member of said group is substituted with up to 4 substituents selected from hydrogen, amino, hydroxyl, hydroxymethyl, methoxy, ethoxy, halogen, $CH_2F$, $CHF_2$, $CF_3$, and aminomethyl, and $R_1$ is selected from a group consisting of aryl, heteroaryl, alkyl, cycloalkyl, heterocycloalkyl, wherein each member of said group is substituted with up to 4 substituents selected from hydrogen, halogen, alkyl, alkenyl, alkynyl, amino, hydroxyl, alkoxy, carboxamido, sulfonyl and cyano.

In other aspects, the present invention provides methods for treating Provirus Integration of Maloney Kinase (PIM Kinase) related disorders in a human or animal subject in need of such treatment comprising administering to said subject an amount of a compound of Formula I or II effective to inhibit PIM activity in the subject.

In other aspects, the present invention provides methods for treating PIM related disorders in a human or animal subject in need of such treatment comprising administering to said subject an amount of a compound of Formula I or II effective to reduce or prevent tumor growth in the subject.

In yet other aspects, the present invention provides methods for treating PIM related disorders in a human or animal subject in need of such treatment comprising administering to said subject an amount of a compound of Formula I or II effective to reduce or prevent tumor growth in the subject in combination with at least one additional agent for the treatment of cancer.

In yet other aspects, the present invention provides therapeutic compositions comprising at least one compound of Formula I or II in combination with one or more additional agents for the treatment of cancer, as are commonly employed in cancer therapy. Yet another aspect provides a pharmaceutical composition further comprising an additional agent for the treatment of cancer, wherein preferably the additional agent is selected from irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, and trastuzumab.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

The invention further provides compositions, methods of use, and methods of manufacture as described in the detailed description of the invention.

DETAILED DESCRIPTION

In accordance with one aspect of the present invention are provided compounds of Formula I:

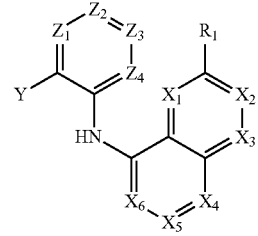

their stereoisomers, tautomers, or pharmaceutically acceptable salts thereof, wherein:

$X_1, X_2, X_3, X_4, X_5$, and $X_6$ are independently selected from $CR_2$ and N, provided that at least one but not more than three of $X_1, X_2, X_3, X_4, X_5$, and $X_6$ are N;

Y is selected from a group consisting of amino, alkoxy, aryl, heteroaryl, partially unsaturated cycloalkyl, cycloalkyl, and heterocycloalkyl, wherein each member of said group is substituted with up to four substituents;

$Z_1, Z_2, Z_3$, and $Z_4$ are independently selected from $CR_{12}$ and N; provided that at least one but not more than two of $Z_1, Z_2, Z_3$, and $Z_4$ are N;

$R_1$ selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino-sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

Another embodiment provides compounds of Formula I, or a stereoisomer, tautomer, or pharmaceutically acceptable salt thereof, wherein $X_1$ is N, $X_2$ and $X_6$ are $CR_2$ or N, and $X_3, X_4$, and $X_5$ are $CR_2$. Provided in another embodiments are compounds of Formula I wherein $Z_3$ is N, and one of, $Z_1, Z_2$, and $Z_4$ are selected from $CR_{12}$ and N, provided that no more than one of $Z_1, Z_2$, and $Z_4$ are N. In some embodiments, compounds of Formula I are provided wherein $X_2$ is N, and $X_6$ is $CR_2$. In yet other embodiments, new compounds of Formula I are provided wherein $Z_3$ is N, and $Z_1, Z_2$, and $Z_4$ are $CR_{12}$.

Yet another embodiment provides compounds of Formula II:

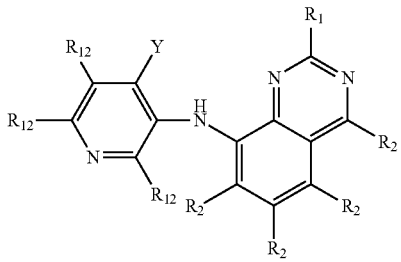

their stereoisomer, tautomer, or pharmaceutically acceptable salt thereof wherein Y is selected from a group consisting of partially unsaturated cycloalkyl, cycloalkyl, and heterocycloalkyl, wherein each of member of said group is substituted with up to 4 substituents selected from hydrogen, halo, alkyl, hydroxyalkyl, haloalkyl, amino, substituted amino, hydroxyl, alkoxy, aryl, heteroaryl and cyano;

$R_1$ is selected from a group consisting of aryl, heteroaryl, alkyl, cycloalkyl, heterocycloalkyl, wherein each member of said group is substituted with up to 4 substituents selected from hydrogen, halogen, alkyl, alkenyl, alkynyl, amino, hydroxyl, alkoxy, carboxamido, sulfonyl and cyano; and $R_2$ and $R_{12}$ independently at each occurrence are selected from the group consisting of hydrogen, halo, hydroxyl, nitro, cyano, $SO_3H$, substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

Another embodiment provides compounds of Formula I or II, their respective stereoisomer, tautomer, or pharmaceutically acceptable salt thereof, wherein $R_2$ and $R_{12}$ are independently selected from hydrogen, halo, hydroxyl, amino, cyano, $C_{1-4}$ alkoxy and $C_{1-4}$ alkyl.

Yet another embodiment provides compounds of Formula I or II, their respective stereoisomer, tautomer, or pharmaceutically acceptable salt thereof, wherein Y is selected from a group consisting of heterocycloalkyl, partially unsaturated cycloalkyl and cycloalkyl, wherein each member of said group is substituted with up to 4 substituents selected from hydrogen, halo, hydroxyl, nitro, cyano, $SO_3H$, substituted or unsubstituted alkyl, alkenyl, alkynyl, alkoxy, amino, cycloalkyl, hetero cycloalkyl, aminocarbonyloxy, amino sulfonyl, aminosulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, heterocycloalkyl, partially saturated cycloalkyl, aryloxy, heteroaryloxy, heterocyclyloxy, cycloalkyloxy, acyl, acylamino and acyloxy, and partially saturated cycloalkyl. In other embodiments, compounds of Formulas I or II are provided wherein Y is selected from a group consisting of piperidinyl, cycloalkyl, partially unsaturated cycloalkyl, piperazinyl, pyrrolidinyl, and azepan, wherein each member of said group is substituted with up to 4 substituents selected from hydrogen, halo, haloalkyl, hydroxyl, cyano, and substituted or unsubstituted alkyl, alkenyl, alkynyl, alkoxy, amino, cycloalkyl, hetero cycloalkyl, aminocarbonyloxy, aminosulfonyl, hydroxyalkyl, aminosulfonyloxy, amino-sulfonylamino, amidino, carboxyl, carboxyl ester, (carboxyl ester)amino, aryl, heteroaryl, aryloxy, heteroaryloxy, heterocyclyloxy, cycloalkyloxy, acyl, acylamino and acyloxy. In yet other embodiments, compounds of Formulas I or II are provided Y is selected from a group consisting of piperidinyl, cyclohexyl, partially unsaturated cyclohexyl, azepane, pyrrolidinyl, and piperazinyl, wherein each member of said group is substituted with up to 4 substituents selected from hydrogen, amino, hydroxyl, hydroxymethyl, methoxy, ethoxy, halogen, $CH_2F$, $CHF_2$, $CF_3$, and aminomethyl, and $R_1$ is selected from a group consisting of aryl, heteroaryl, alkyl, cycloalkyl, heterocycloalkyl, wherein each member of said group is substituted with up to 4 substituents selected from hydrogen, halogen, alkyl, alkenyl, alkynyl, amino, hydroxyl, alkoxy, carboxamido, sulfonyl and cyano.

In some presently preferred aspects, the present invention provides new compounds selected from the group consisting of N-(4-(3-aminocyclohex-1-enyl)pyridin-3-yl)-2-(2,6-difluorophenyl)quinazolin-8-amine, (3R,4S)-3-amino-1-(3-(2-(2,6-difluoro-phenyl)quinazolin-8-ylamino)pyridin-4-yl)piperidin-4-ol, (3R,4R)-3-amino-1-(3-(2-(2,6-difluorophenyl)quinazolin-8-ylamino)pyridin-4-yl)piperidin-4-ol, (3R,5S)-5-amino-1-(3-(2-(2,6-difluorophenyl)quinolin-8-ylamino)pyridin-4-yl)piperidin-3-ol, ((3R,5S)-5-amino-1-(3-(2-(2,6-difluorophenyl)quinolin-8-ylamino)pyridin-4-yl)piperidin-3-yl)-methanol, N-(4-((3S,5R)-3-amino-5-ethoxypiperidin-1-yl)pyridin-3-yl)-2-(2,6-difluoro-phenyl)quinazolin-8-amine, (R)—N-(4-(3-aminopiperidin-1-yl)pyridin-3-yl)-2-(2,6-difluorophenyl)quinazolin-8-amine, 1-(3-(2-(2,6-difluorophenyl)quinazolin-8-ylamino)-pyridin-4-yl)piperidine-3,5-diamine, N-(4-((3R,4R)-3-amino-4-fluoropiperidin-1-yl)-pyridin-3-yl)-2-(2,6-difluorophenyl)quinazolin-8-amine, N-(4-((3S,4S)-3-amino-4-fluoropiperidin-1-yl)pyridin-3-yl)-2-(2,6-difluorophenyl)quinazolin-8-amine, N-(4-(3-amino-azepan-1-yl)pyridin-3-yl)-2-(2,6-difluorophenyl)quinazolin-8-amine, (S)—N-(4-(3-amino-piperidin-1-yl)pyrimidin-5-yl)-2-(2,6-difluorophenyl)quinazolin-8-amine, N-(4-((3S,5R)-3-amino-5-(fluoromethyl)piperidin-1-yl)pyridin-3-yl)-2-(2,6-difluorophenyl)quinazolin-8-amine, N-(4-((3R,5S)-3-amino-5-methylpiperidin-1-yl)pyridin-3-yl)-2-(2,6-difluoro-phenyl)quinazolin-8-amine, N-(4-((3S,5R)-3-amino-5-methylpiperidin-1-yl)pyridin-3-yl)-2-(2,6-difluorophenyl)quinazolin-8-amine, (S)—N-(4-(3-aminopiperidin-1-yl)pyridin-3-yl)-2-(thiazol-2-yl)quinazolin-8-amine, (S)—N-(4-(3-aminopiperidin-1-yl)pyridin-3-yl)-2-(2,6-difluorophenyl)quinazolin-8-amine, (S)—N-(4-(3-aminopiperidin-1-yl)pyridin-3-yl)-2-(3-(thiazol-2-yl)phenyl)quinazolin-8-amine and (S)—N-(4-(3-aminopiperidin-1-yl)pyridin-3-yl)-2-(2-fluorophenyl)quinazolin-8-amine, or a stereoisomer, tautomer, or pharmaceutically acceptable salt thereof. In other presently preferred aspects, the present invention provides new compounds selected from the group consisting of (3R,4S)-3-amino-1-(3-(2-(2,6-difluorophenyl)quinazolin-8-ylamino)pyridin-4-yl)piperidin-4-ol, (3R,4R)-3-amino-1-(3-(2-(2,6-difluorophenyl)quinazolin-8-ylamino)pyridin-4-yl)-piperidin-4-ol, (3R,5S)-5-amino-1-(3-(2-(2,6-difluorophenyl)quinolin-8-ylamino)pyridin-4-yl)piperidin-3-ol, ((3R,5S)-5-amino-1-(3-(2-(2,6-difluorophenyl)quinolin-8-ylamino)-pyridin-4-yl)piperidin-3-yl)methanol, N-(4-((3R,4R)-3-amino-4-fluoropiperidin-1-yl)-pyridin-3-yl)-2-(2,6-difluorophenyl)quinazolin-8-amine, N-(4-((3S,5R)-3-amino-5-(fluoromethyl)piperidin-1-yl)pyridin-3-yl)-2-(2,6-difluorophenyl)quinazolin-8-amine, N-(4-((3R,5S)-3-amino-5-methylpiperidin-1-yl)pyridin-3-yl)-2-

(2,6-difluorophenyl)-quinazolin-8-amine, N-(4-((3S,5R)-3-amino-5-methylpiperidin-1-yl)pyridin-3-yl)-2-(2,6-difluorophenyl)quinazolin-8-amine, (S)—N-(4-(3-aminopiperidin-1-yl)pyridin-3-yl)-2-(thiazol-2-yl)quinazolin-8-amine, (S)—N-(4-(3-aminopiperidin-1-yl)pyridin-3-yl)-2-(2,6-difluorophenyl)quinazolin-8-amine and (S)—N-(4-(3-aminopiperidin-1-yl)pyridin-3-yl)-2-(2-fluorophenyl)quinazolin-8-amine, or a stereoisomer, tautomer, or pharmaceutically acceptable salt thereof.

In other aspects, the present invention provides methods for treating Provirus Integration of Maloney Kinase (PIM Kinase) related disorders in a human or animal subject in need of such treatment comprising administering to said subject an amount of a compound of Formula I or II effective to inhibit PIM activity in the subject.

In other aspects, the present invention provides methods for treating PIM related disorders in a human or animal subject in need of such treatment comprising administering to said subject an amount of a compound of Formula I or II effective to reduce or prevent tumor growth in the subject.

In yet other aspects, the present invention provides methods for treating PIM related disorders in a human or animal subject in need of such treatment comprising administering to said subject an amount of a compound of Formula I or II effective to reduce or prevent tumor growth in the subject in combination with at least one additional agent for the treatment of cancer. Yet another aspect provides a pharmaceutical composition further comprising an additional agent for the treatment of cancer, wherein preferably the additional agent is selected from irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, and trastuzumab.

In yet other aspects, the present invention provides therapeutic compositions comprising at least one compound of Formula I or II in combination with one or more additional agents for the treatment of cancer, as are commonly employed in cancer therapy.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

The invention further provides pharmaceutical compositions comprising an amount of a compound of Formula I or II effective to inhibit Kinase activity in a human or animal patient when administered thereto, methods of use of compounds of Formula I or II in the treatment of PIM Kinase mediated disorders, and methods of manufacture as described in the detailed description of the invention.

DEFINITIONS

"PIM inhibitor" is used herein to refer to a compound that exhibits an $IC_{50}$ with respect to PIM Kinase activity of no more than about 100 µM and more typically not more than about 50 µM, as measured in the PIM depletion assays described hereinbelow.

The phrase "alkyl" refers to a straight chain saturated group containing $C_{1-10}$ carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase alkyl also includes branched $C_{3-8}$ alkyl groups, including but not limited to, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and the like. The term "loweralkyl" refers to an alkyl group containing from 1 to 5 carbon atoms. Thus the phrase alkyl groups includes primary alkyl groups, secondary alkyl groups, and tertiary alkyl groups. Preferred alkyl groups include straight and branched chain alkyl groups having 1 to 6 carbon atoms.

As used herein, the term "halogen" or "halo" refers to chloro, bromo, fluoro and iodo groups. "Haloalkyl" refers to an alkyl group wherein one or more hydrogen atoms is replaced with one or more halogen atoms. The term "haloalkoxy" refers to an alkoxy group substituted with one or more halogen atoms.

"Amino" refers herein to the group —NH$_2$. The term "alkylamino" refers to the group —NRR' where R and R' are each independently selected from hydrogen and alkyl. The term "arylamino" refers herein to the group —NR"R' wherein R" is aryl and R' is hydrogen, alkyl, or an aryl. The term "aralkylamino" refers herein to the group —NRR' where R is aralkyl and R' is hydrogen, alkyl, an aryl, or a aralkyl. The term cyano refers to the group —CN. The term nitro refers to the group —NO$_2$.

The term "alkoxyalkyl" refers to the group -alk$_1$-O-alk$_2$ where alk$_1$ is alkyl or alkenyl, and alk$_2$ is alkyl or alkenyl.

The term "aminocarbonyl" refers herein to the group —C(O)—NH$_2$. "Substituted aminocarbonyl" refers herein to the group —C(O)—NRR' where R is alkyl and R' is hydrogen or a loweralkyl. In some embodiments, R and R', together with the N atom attached to them may be taken together to form a "heterocycloalkylcarbonyl" group. The term "arylaminocarbonyl" refers herein to the group —C(O)—NRR' where R is an aryl and R' is hydrogen, alkyl or aryl. The term "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—NH$_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group-aryl-S(O)$_2$—NH-aralkyl, where the aralkyl is loweraralkyl.

"Carbonyl" refers to the divalent group —C(O)—. "Carboxy" refers to —C(=O)—OH. "Alkoxycarbonyl" refers to ester —C(=O)—OR wherein R is alkyl. "Loweralkoxycarbonyl" refers to ester —C(=O)—OR wherein R is loweralkyl. "Cycloalkyloxycarbonyl" refers to —C(=O)—OR wherein R is cycloalkyl. "Aryloxycarbonyl" refers to —C(=O)—OR wherein R is aryl. "Heterocyclyloxycarbonyl" refers to —C(=O)—OR wherein R is heterocyclyl.

The term "aralkoxycarbonyl" refers herein to the group —C(O)—O-aralkyl, where the aralkyl is loweraralkyl.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—R, where R is a straight or branched chain loweralkyl, cycloalkyl, or aryl or loweraralkyl.

"Cycloalkyl" refers to a mono- or polycyclic, carbocyclic alkyl substituent. Typical cycloalkyl substituents have from 3 to 8 ring carbon atoms. Carbocycloalkyl groups are cycloalkyl groups in which all ring atoms are carbon. Illustrative examples of cycloalkyl group are cyclohexyl, cyclopentyl, cyclopropyl, cyclobutyl, and the like. When used in connection with cycloalkyl substituents, the term "polycyclic" refers herein to fused and non-fused alkyl cyclic structures. Illustratrive examples of a polycyclic cycloalkyl group are octahydro-1H-indene, bicyclo[4.2.0]octane, bicyclo[3.2.0]heptane, spiro[3.3]heptane, and the like. The term partially unsaturated cycloalkyl group refers to a cycloalkyl group as defined above, wherein at least two adjacent carbon atoms of the cycloalkyl group are connected to each other by a double or a triple bond. Illustrative examples of partially unsaturated cycloalkyl groups include cyclopentenyl, cyclopentynyl, cyclohexenyl, cyclohexynyl, and the like.

The term "heterocycle" or "heterocyclic group" or "heterocycloalkyl" as used herein refers to a 4 to 10 membered cyclic ring system wherein atleast one but not more than five members of the ring system is a heteroatom selected from nitrogen, oxygen, and sulfur. A preferred heterocyclic group is a 5 to 9 membered cyclic ring system wherein from one to three members of the ring system are heteroatoms selected from the group consisting of nitrogen, oxygen, and sulfur. It should be noted that the nitrogen and sulfur atom contained within the heterocyclic ring systems maybe optionally oxidized as well as optionally quarternized. It is further understood that the term heterocycle, or heterocyclic group, or heterocycle, as used herein can include a single or multiple double or triple bonds. Illustrative examples of the heterocyclic group are piperidinyl, 1,2,3,4-tetrahydropyridine, tetrahydropyran, 3,6-dihydro-2H-pyran, tertahydrofuran, piperidine, and the like.

Heterocyclic moieties can be unsubstituted or monosubstituted or disubstituted with various substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

Representative heterocyclics include, for example, imidazolyl, pyridyl, piperazinyl, piperidinyl, azetidinyl, pyrrodynyl, azepan, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 5 to 10 membered ring systems. Illustrative examples of aryl groups are phenyl, naphthyl, and the like. The term "heteroaryl" as used herein represents 5 to 12 membered cyclic aromatic structures wherein from 1 to about 6 members are heteroatoms selected from N, O, and S. Illustrative examples of a heteroaryl group are pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

"Optionally substituted" or "substituted" refers to the replacement of one or more hydrogen atoms with a monovalent or divalent radical. Suitable substitution groups include, for example, hydroxy, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkylamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxy, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The compounds of the invention, or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)— or (S)— forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compounds of Formulas (I), (II), (III) or (IV). These salts can be prepared in situ during the final isolation and purification of the compounds of Formulas (I), (II), (III) or (IV), or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The invention further provides deuterated versions of the above-described compounds. As used herein, "deuterated version" refers to a compound in which at least one hydrogen atom is enriched in the isotope deuterium beyond the natural rate of deuterium occurrence. Typically, the hydrogen atom is enriched to be at least 50% deuterium, frequently at least 75% deuterium, and preferably at least about 90% deuterium. Optionally, more than one hydrogen atom can be replaced by deuterium. For example, a methyl group can be deuterated by replacement of one hydrogen with deuterium (i.e., it can be —CH$_2$D), or it can have all three hydrogen atoms replaced with deuterium (i.e., it can be —CD$_3$). In each case, D signifies that at least 50% of the corresponding H is present as deuterium.

It will be apparent to those skilled in the art that the compounds of the invention, or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formula (I) or their tautomers, prodrugs and stereoisomers, as well as the pharmaceutically acceptable salts, esters and prodrugs of any of them, are included within the invention. The term "cancer" refers to cancer diseases that can be beneficially treated by the inhibition of Pim kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma and erythroleukemia), adenomas (e.g., villous colon adenoma) and sarcomas (e.g., osteosarcoma).

Synthetic Methods

The compounds of the invention can be obtained through procedures known to the skilled in the art. For example, as shown in Scheme 1,4-chloro, 3-nitro pyridine can be reacted with a nucleophile yielding after nitro reduction a 4-substituted 3-amino pyridine I. The substituted amino pyridines I can react with quinazoline derived triflate by Buchwald reaction condition to give 3, 4 disubstituted pyridines II.

Scheme 1.

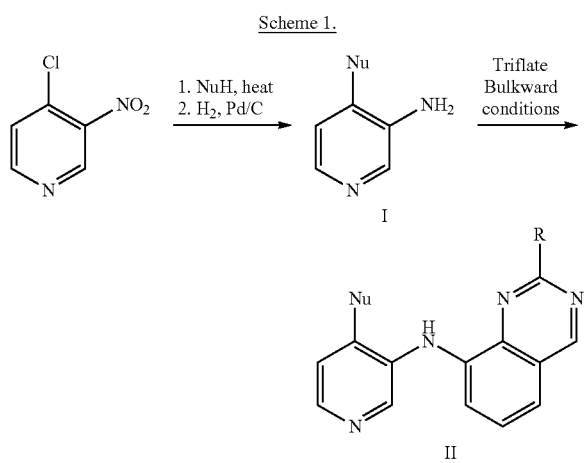

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Pim activity by any of the assays described herein, by other Pim kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in *Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In one embodiment, the invention provides a method of inhibiting Pim1, Pim2 or Pim3 in a human or animal subject. The method includes administering an effective amount of a compound, or a pharmaceutically acceptable salt thereof, of any of the embodiments of compounds of formula (I), (II), (III) or (IV) to a subject in need thereof.

The present invention will be understood more readily by reference to the following examples, which are provided by way of illustration and are not intended to be limiting of the present invention.

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY HPLC system and a ZQ 2000 system; Column: ACQUITY HPLC HSS—C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

Nuclear magnetic resonance (NMR) analysis was performed on some of the compounds with a Varian 300 MHz NMR (Palo Alto, Calif.). The spectral reference was either TMS or the known chemical shift of the solvent.

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings

ABBREVIATIONS

| | |
|---|---|
| DAST | (diethylamino)sulfurtrifluoride |
| DCM | dichloromethane |
| DIEA | diisopropylethylamine |
| DMA | dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | Ethyl dimethylaminopropylazodicarboxylate hydrochloride |
| EtOAc | ethyl acetate |
| EtOH | Ethanol |
| HOAT | Hydroxyazabenzotriazole |
| $K_2CO_3$ | Potassium carbonate |
| MeCN | acetonitrile |
| $MgSO_4$ | Magnesium sulfate |
| MeOH | methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II)-dichloromothehane adduct |
| RT or rt | room temperature |
| TDMSCl | tert-butyldimethylsilylchloride |
| TEA | triethylamine |
| THF | tetrahydrofuran |

Method 1

Synthesis of 3-nitro-4-(piperidin-1-yl)pyridine

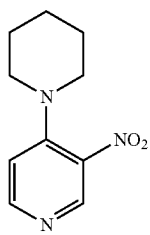 [SMILES: O=[N+]([O-])c1cnccc1N1CCCCC1]

A solution of 4-chloro-3-nitropyridine (1.0 equiv.) and piperidine (2.0 equiv.) in ethanol, at a concentration of 0.5 M, was stirred at rt for 48 hours at which time the ethanol was removed in vacuo. The residue was partitioned between EtOAc (300 mL) and $Na_2CO_3$ $_{(sat.)}$ (75 mL), was washed further with $H_2O$ (50 mL), $NaCl_{(sat.)}$ (50 mL), was dried over $MgSO_4$, was filtered and the volatiles were removed in vacuo yielding 3-nitro-4-(piperidin-1-yl)pyridine (95%). LCMS (m/z): 207.7 ($MH^+$); LC $R_t$=1.60 min. $^1H$ NMR ($CDCl_3$): δ 8.80 (s, 1H), 8.31 (d, J=5.7, 1H), 6.84 (d, J=6.3, 1H), 3.18-3.21 (m, 4H), 1.64-1.78 (m, 6H).

Synthesis of 4-(piperidin-1-yl)pyridin-3-amine

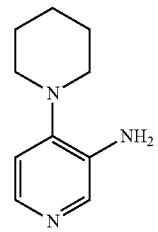

To a solution of 3-nitro-4-(piperidin-1-yl)pyridine (1.0 equiv.) in ethanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding 4-(piperidin-1-yl)pyridin-3-amine (93%) as an oil. LCMS (m/z): 178.0 ($MH^+$); LC $R_t$=1.68 min. $^1H$ NMR ($CDCl_3$): δ 8.01 (s, 1H), 7.96 (d, J=5.4, 1H), 6.78 (d, J=5.1, 1H), 3.64-3.74 (m, 2H), 2.86-2.94 (m, 4H), 1.66-1.78 (m, 4H), 1.58-1.64 (m, 2H).

Synthesis of trans (+/−)-Benzyl 3-(tert-butoxycarbonylamino)-4-hydroxypiperidine-1-carboxylate

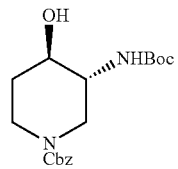 [SMILES: CC(C)(C)OC(=O)N[C@@H]1CN(C(=O)OCc2ccccc2)CC[C@H]1O]

Synthesis of trans (+/−)-Benzyl 4-(tert-butoxycarbonylamino)-3-hydroxypiperidine-1-carboxylate

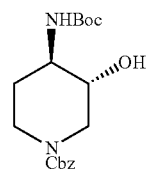

A solution of (+/−) benzyl 7-oxa-3-azabicyclo[4.1.0]heptane-3-carboxylate (1.0 equiv.) in saturated ammonium hydroxide aqueous solution and ethanol (1:1, 0.05 M solution) in a sealed steel bomb was heated to 70° C. for 5 h. After all volatile materials were removed by $N_2$ gas stream, ethyl acetate and water were added for work-up. The crude regioisomeric mixture, benzyl 3-amino-4-hydroxypiperidine-1-carboxylate and benzyl 4-amino-3-hydroxypiperidine-1-carboxylate was reacted with $Boc_2O$ (1.0 equiv.) and triethylamine (1.0 equiv.) in dichloromethane (0.1 M solution). After stirred for 2 h at room temperature, the reaction mixture was extracted with dichloromethane. The polar (+/−)-benzyl 3-(tert-butoxycarbonylamino)-4-hydroxy-piperidine-1-carboxylate and nonpolar (+/−)-benzyl 4-(tert-butoxycarbonylamino)-3-hydroxypiperidine-1-carboxylate were obtained by flash column chromatography (20% to 40% EtOAc in hexanes, 28%, 51% each). LCMS (m/z): 351.1 (MH+), R$_t$=0.81 min, LCMS (m/z): 351.1 (MH+), R$_t$=0.83 min. The enantiomerically pure (3S,4S)-benzyl 3-(tert-butoxycarbonylamino)-4-hydroxypiperidine-1-carboxylate and (3R,4R)-benzyl 3-(tert-butoxycarbonylamino)-4-hydroxypiperidine-1-carboxylate were resolved by chiral HPLC (For analysis R$_t$=6.8 min and 9.1 min respectively; n-heptane:ethanol=70:30 (v:v), Chiralpak AD-H prep 250×4.6 mm at 1 mL/min. For preparative separation, n-heptane:ethanol=80:20 (v:v), Chiralpak AS 50×500 mm at 90 mL/min).

Synthesis of (3R,4R)-benzyl 3-(tert-butoxycarbonylamino)-4-(methylsulfonyloxy)-piperidine-1-carboxylate

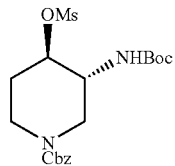 [SMILES: CC(C)(C)OC(=O)N[C@@H]1CN(C(=O)OCc2ccccc2)CC[C@H]1OS(C)(=O)=O]

To a solution of (3R,4R)-benzyl 3-(tert-butoxycarbonylamino)-4-hydroxypiperidine-1-carboxylate in dichloromethane (0.13 M) was added triethylamine (1.5 equiv.) followed by methanesulfonyl chloride (1.3 equiv.). The reaction was allowed to stir at room temperature for 15 h. The solution was then quenched with saturated NaHCO$_3$, extracted with dichloromethane, dried with sodium sulfate, and concentrated to give the crude (3R,4R)-benzyl 3-(tert-butoxycarbonylamino)-4-(methylsulfonyl-oxy)piperidine-1-carboxylate in >95% yield. LCMS (m/z): 428.9/328.9 (MH+), R$_t$=3.81 min.

Synthesis of (3aR,7aS)-benzyl 2-oxohexahydrooxazolo[4,5-c]pyridine-5(6H)-carboxylate

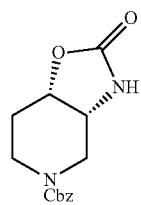 [SMILES: O=C1N[C@@H]2CN(C(=O)OCc3ccccc3)CC[C@@H]2O1]

A solution of (3R,4R)-benzyl 3-(tert-butoxycarbonylamino)-4-(methylsulfonyloxy)piperidine-1-carboxylate in pyridine (0.16 M) was heated to 120° C. in the microwave for 10 minutes. The solution was then concentrated to almost dryness and the forming solid was filtered to give the desired product. The filtrate was further purified via silica gel column chromatography eluting with ethyl acetate (100%) to yield (3aR,7aS)-benzyl 2-oxohexahydrooxazolo[4,5-c]pyridine-5(6H)-carboxylate in 75% combined yield. LCMS (m/z): 277.1 (MH+), R$_t$=2.327 min.

Synthesis of (3aR,7aS)-5-benzyl 3-tert-butyl 2-oxotetrahydro-oxazolo[4,5-c]pyridine-3,5(2H,6H)-dicarboxylate

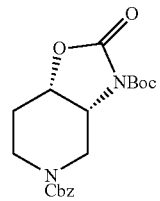 [SMILES: CC(C)(C)OC(=O)N1C(=O)O[C@H]2CCN(C(=O)OCc3ccccc3)C[C@H]21]

To a solution of (3aR,7aS)-benzyl 2-oxohexahydrooxazolo[4,5-c]pyridine-5(6H)-carboxylate (1.0 equiv.) in dichloromethane (0.09 M) was added BOC$_2$O (1.1 equiv.), triethylamine (1.1 equiv.), and a catalytic amount of DMAP. The reaction was stirred at room temperature for one hour at which point it was concentrated under vacuo and filtered through a plug of silica gel eluting with ethylacetate. The product was dried under vacuo to yield (3aR,7aS)-5-benzyl 3-tert-butyl 2-oxotetra-hydrooxazolo[4,5-c]pyridine-3,5 (2H,6H)-dicarboxylate_as a white solid in 75% yield. LCMS (m/z): 277.2 (MH+), R$_t$=3.43 min.

Synthesis of (3aR,7aS)-tert-butyl 5-(3-nitropyridin-4-yl)-2-oxohexahydro-oxazolo[4,5-c]pyridine-3(2H)-carboxylate

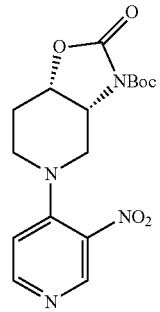 [SMILES: CC(C)(C)OC(=O)N1C(=O)O[C@H]2CCN(c3ccncc3[N+](=O)[O-])C[C@H]21]

To a solution of (3aR,7aS)-5-benzyl 3-tert-butyl 2-oxotetrahydrooxazolo[4,5-c]pyridine-3,5(2H,6H)-dicarboxylate in a mixture of EtOH and EtOAc (1:1, 0.07 M) was added Pd/C (10% by weight) and the reaction was stirred under a hydrogen balloon for 15 h. The solution was then filtered through a pad of Celite and the filtrate was concentrated to dryness to give a clear oil. To a solution of (3aR,7aS)-tert-butyl 2-oxohexahydrooxazolo[4,5-c]pyridine-3(2H)-carboxylate in i-PrOH (0.12 M) was added 4-chloro-3-nitropyridine (1.2 equiv.) and DIEA (4.0 equiv.) The reaction was heated to 75° C. for 2 h, then cooled to room temperature and concentrated under vacuo. The crude mixture was diluted with EtOAc, water was added, the organic layer was extracted, washed with brine, dried with Na$_2$SO$_4$, and concentrated. The crude was purified via silica gel column chromatography eluting with EtOAc (100%) to yield (3aR,7aS)-tert-butyl 5-(3-nitropyridin-4-yl)-2-oxohexahydrooxazolo[4,5-c]pyridine-3

(2H)-carboxylate as a yellow foam in 89% yield. LCMS (m/z): 365.1 (MH⁺), $R_t$=1.79 min.

Synthesis of (3aR,7aS)-tert-butyl 5-(3-aminopyridin-4-yl)-2-oxohexahydro-oxazolo[4,5-c]pyridine-3(2H)-carboxylate

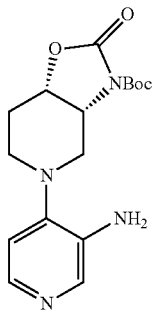

To a solution of (3aR,7aS)-tert-butyl 5-(3-nitropyridin-4-yl)-2-oxohexahydrooxazolo[4,5-c]pyridine-3(2H)-carboxylate in EtOH and EtOAc (1:1, 0.15 M) was added Pd/C (10% by weight) and the reaction was stirred under a hydrogen balloon for 15 h. The solution was filtered through a pad of Celite, and the filtrate was concentrated to yield (3aR,7aS)-tert-butyl 5-(3-aminopyridin-4-yl)-2-oxohexahydrooxazolo[4,5-c]pyridine-3(2H)-carboxylate_as a clear oil in >95% yield. LCMS (m/z): 335.0 (MH⁺), $R_t$=1.681 min.

Synthesis of (3R,4R)-benzyl 3-(tert-butoxycarbonylamino)-4-(tert-butyldimethylsilyloxy)piperidine-1-carboxylate

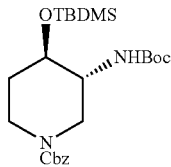 [SMILES: CC(C)(C)OC(=O)N[C@@H]1CN(C(=O)OCc2ccccc2)CC[C@H]1O[Si](C)(C)C(C)(C)C]

To a solution of (3R,4R)-benzyl 3-(tert-butoxycarbonylamino)-4-hydroxypiperidine-1-carboxylate (1.0 equiv.) in dichloromethane (0.1 M solution) was added imidazole (1.1 equiv.), DMAP (0.1 equiv.), and TBDMSCl (1.1 equiv.) sequentially. The reaction mixture was stirred at room temperature for 20 h. After worked up with dichloromethane, the crude material was purified by silica column chromatography (10% to 20% EtOAc in hexanes) yielding (3R,4R)-benzyl 3-(tert-butoxycarbonylamino)-4-(tert-butyldimethylsilyloxy)piperidine-1-carboxylate (76%). LCMS (m/z): 365.2 [(M-Boc)H⁺]; LC $R_t$=6.05 min.

Synthesis of tert-butyl (3R,4R)-4-(tert-butyldimethylsilyloxy)piperidin-3-ylcarbamate

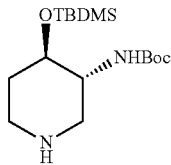 [SMILES: CC(C)(C)OC(=O)N[C@@H]1CNCC[C@H]1O[Si](C)(C)C(C)(C)C]

Method 1 was followed using (3R,4R)-benzyl 3-(tert-butoxycarbonylamino)-4-(tert-butyldimethylsilyloxy)piperidine-1-carboxylate (1.0 equiv.) yielding crude tert-butyl (3R,4R)-4-(tert-butyldimethylsilyloxy)piperidin-3-ylcarbamate, (>99%). LCMS (m/z): 331.3 (MH⁺).

Synthesis of tert-butyl (3R,4R)-4-(tert-butyldimethylsilyloxy)-1-(3-nitropyridin-4-yl)piperidin-3-ylcarbamate

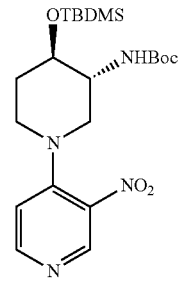

Method 1 was followed using 1 eq each of 4-chloro-3-nitropyidine, tert-butyl (3R,4R)-4-(tert-butyldimethylsilyloxy)piperidin-3-ylcarbamate and triethylamine in DMF yielding tert-butyl (3R,4R)-4-(tert-butyldimethylsilyloxy)-1-(3-nitropyridin-4-yl)piperidin-3-ylcarbamate, (98%). LCMS (m/z): 453.3 (MH⁺); LC $R_t$=4.01 min.

Synthesis of tert-butyl (3R,4R)-1-(3-aminopyridin-4-yl)-4-(tert-butyldimethylsilyloxy)-piperidin-3-ylcarbamate

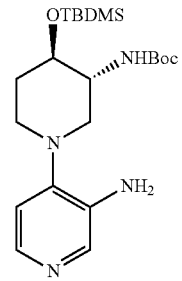 [SMILES: CC(C)(C)OC(=O)N[C@@H]1CN(c2ccncc2[N+](=O)[O-])CC[C@H]1O[Si](C)(C)C(C)(C)C]

Following method 1, tert-butyl (3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-(tert-butyldimethylsilyloxy)piperidin-3-ylcarbamate, (>99%). LCMS (m/z): 423.2 (MH⁺); LC $R_t$=3.78 min.

Synthesis of (3R,4R)-Benzyl 3-(tert-butoxycarbonylamino)-4-fluoropiperidine-1-carboxylate and (3S,4S)-Benzyl 3-(tert-butoxycarbonylamino)-4-fluoropiperidine-1-carboxylate

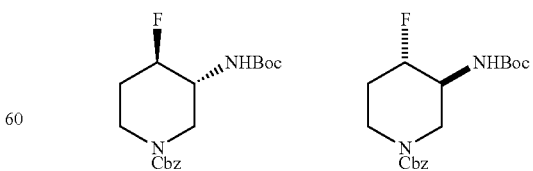

To a solution of (+/−)-benzyl 3-(tert-butoxycarbonylamino)-4-hydroxypiperidine-1-carboxylate (1.0 equiv.) in dichloromethane (0.3 M solution) was added DAST at −78° C. The reaction mixture was slowly warmed up to room temperature for 15 h. After quenched with saturated sodium bicarbonate aqueous solution, ethyl acetate and water were added for work-up. The (+/−)-benzyl 3-(tert-butoxycarbonylamino)-4-fluoropiperidine-1-carboxylate was obtained by silica column chromatography (30% EtOAc in hexanes, 40%). LCMS (m/z): 253.1[(M-Boc)H$^+$]; LC R$_t$=4.08 min. The enantiomerically pure (3R,4R)-benzyl 3-(tert-butoxycarbonylamino)-4-fluoropiperidine-1-carboxylate and (3S,4S)-benzyl 3-(tert-butoxycarbonylamino)-4-fluoropiperidine-1-carboxylate were resolved by chiral HPLC (for analysis: R$_t$=9.4 min and 12.6 min respectively; n-heptane:isopropanol=90:10 (v:v), Chiralpak AS 250×4.6 mm at 1 mL/min. For preparative separation, n-heptane:isopropanol=90:10 (v:v), Chiralpak AS 50×500 mm at 90 mL/min).

Synthesis of tert-butyl (3R,4R)-4-fluoropiperidin-3-ylcarbamate

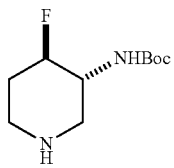 [SMILES: CC(C)(C)OC(=O)N[C@@H]1CNCC[C@H]1F]

Method 1 was followed using (3R,4R)-benzyl 3-(tert-butoxycarbonylamino)-4-fluoropiperidine-1-carboxylate (1.0 equiv.) yielding crude tert-butyl (3R,4R)-4-fluoropiperidin-3-ylcarbamate, (93%). LCMS (m/z): 219.2 (MH$^+$), LC R$_t$=0.45 min.

Synthesis of tert-butyl (3S,4S)-4-fluoropiperidin-3-ylcarbamate

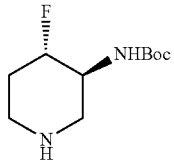 [SMILES: CC(C)(C)OC(=O)N[C@H]1CNCC[C@@H]1F]

Method 1 was followed using (3S,4S)-benzyl 3-(tert-butoxycarbonylamino)-4-fluoropiperidine-1-carboxylate (1.0 equiv.) yielding crude (+/−)-tet-butyl 4-fluoropiperidin-3-ylcarbamate, (93%). LCMS (m/z): 219.2 (MH$^+$), LC R$_t$=0.45 min.

Synthesis of tert-butyl (3R,4R)-4-fluoro-1-(3-nitropyridin-4-yl)piperidin-3-ylcarbamate

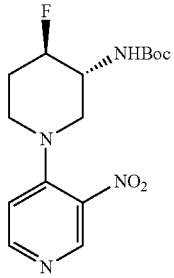 [SMILES: CC(C)(C)OC(=O)N[C@@H]1CN(c2ccncc2[N+](=O)[O-])CC[C@H]1F]

Method 1 was followed using 1 eq each of 4-chloro-3-nitropyidine, tert-butyl (3R,4R)-4-fluoropiperidin-3-ylcarbamate and triethylamine in ethanol yielding tert-butyl (3R,4R)-4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl (3S,4S)-4-fluoro-1-(3-nitropyridin-4-yl)piperidin-3-ylcarbamate

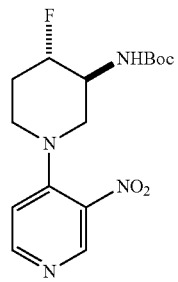

Method 1 was followed using 1 eq each of 4-chloro-3-nitropyidine, tert-butyl (3S,4S)-4-fluoropiperidin-3-ylcarbamate and triethylamine in ethanol yielding tert-butyl (3S,4S)-4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl (3R,4R)-1-(3-aminopyridin-4-yl)-4-(tert-butyldimethylsilyloxy)-piperidin-3-ylcarbamate

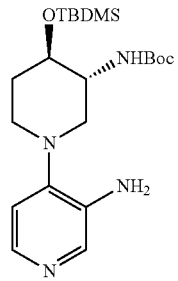

Following method 1, tert-butyl (3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-(tert-butyldimethylsilyloxy)piperidin-3-ylcarbamate, (>99%). LCMS (m/z): 423.2 (MH$^+$); LC R$_t$=3.78 min.

Synthesis of tert-butyl (3S,4S)-1-(3-aminopyridin-4-yl)-4-(tert-butyldimethylsilyloxy)-piperidin-3-ylcarbamate

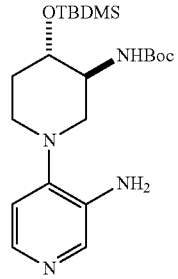 [SMILES: CC(C)(C)OC(=O)N[C@H]1CN(c2ccncc2N)CC[C@@H]1O[Si](C)(C)C(C)(C)C]

Following method 1, tert-butyl (3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-(tert-butyldimethylsilyloxy)piperidin-3-ylcarbamate, (>99%). LCMS (m/z): 423.2 (MH$^+$); LC R$_t$=3.78 min.

Synthesis of tert-butyl (3R,4R)-1-(3-aminopyridin-4-yl)-4-fluoropiperidin-3-ylcarbamate

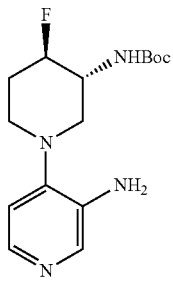 [SMILES: CC(C)(C)OC(=O)N[C@@H]1CN(c2ccncc2N)CC[C@H]1F]

Following method 1, tert-butyl (3R,4R)-4-fluoro-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-fluoropiperidin-3-ylcarbamate, (>99%). LCMS (m/z): 311.2 (MH$^+$); LC R$_t$=2.14 min.

Synthesis of tert-butyl (3S,4S)-1-(3-aminopyridin-4-yl)-4-fluoropiperidin-3-ylcarbamate

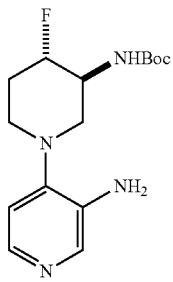

Following method 1, tert-butyl (3S,4S)-4-fluoro-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-fluoropiperidin-3-ylcarbamate, (>99%). LCMS (m/z): 311.2 (MH$^+$); LC R$_t$=2.14 min.

Synthesis of cis-(+/−)-1-(benzyloxycarbonyl)-5-(tert-butoxycarbonylamino)-piperidine-3-carboxylic acid

To a solution of cis-(+/−)-5-(tert-butoxycarbonylamino) piperidine-3-carboxylic acid (1.0 eq.) in dichloromethane (0.2 M) was added DIEA(1.1 eq.), followed by N-(benzyloxycarbonyloxy)succinimide (1.0 eq.); the reaction was stirred at r.t. overnight. The solvent was removed under reduced pressure. To the crude was added EtOAc and 1N HCl. After extraction, the organic layer was washed with brine, dried and filtered, and concentrated to yield cis-(+/−)-1-(benzyloxycarbonyl)-5-(tert-butoxy-carbonylamino)piperidine-3-carboxylic acid (99% yield) LCMS (m/z): 379.2 (MH$^+$); LC R$_t$=3.55 min.

Synthesis of cis-(+/−)-benzyl 3,5-bis(tert-butoxycarbonylamino)piperidine-1-carboxylate

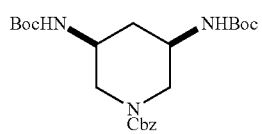 [SMILES: CC(C)(C)OC(=O)N[C@@H]1C[C@H](NC(=O)OC(C)(C)C)CN(C(=O)OCc2ccccc2)C1]

To a solution of cis-(+/−)-1-(benzyloxycarbonyl)-5-(tert-butoxycarbonylamino) piperidine-3-carboxylic acid (1.2 g, 3.17 mmol), DPPA (Diphenylphosphoryl azide, 1.04 g, 3.81 mmol) and DIEA(1.1 mL, 6.35 mmol) in t-BuOH(10 mL) was heated to 90° C. over night. The solvent was removed under reduced pressure. To the crude was added EtOAc (300 mL), the organic layer was washed with saturated NaHCO$_3$ (150 mL) and brine, dried and filtered, and concentrated to give the crude. The crude material was further purified by silica gel chromatography to yielding cis-(+/−)-benzyl 3,5-bis(tert-butoxycarbonylamino)piperidine-1-carboxylate, (23%). LCMS (m/z): 350(minus one Boc(MH$^+$); LC R$_t$=4.40 min.

Synthesis of tert-butyl cis-(+/−)-piperidine-3,5-diyl-dicarbamate

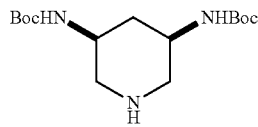 [SMILES: CC(C)(C)OC(=O)N[C@@H]1CNC[C@H](NC(=O)OC(C)(C)C)C1]

Method 1 was followed using cis-(+/−)-benzyl 3,5-bis(tert-butoxycarbonylamino)piperidine-1-carboxylate yielding tert-butyl cis-(+/−)-piperidine-3,5-diyldicarbamate, (% yield 99%). LCMS (m/z): 316.2 (MH$^+$).

Synthesis of tert-butyl cis-(+/−)-1-(3-nitropyridin-4-yl)piperidine-3,5-diyldicarbamate

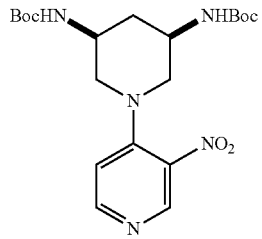 [SMILES: CC(C)(C)OC(=O)N[C@@H]1C[C@H](NC(=O)OC(C)(C)C)CN(c2ccncc2[N+](=O)[O-])C1]

Method 1 was followed using 1 equivalent each of 4-chloro-3-nitropyridine, tert-butyl cis-(+/−)-piperidine-3,5-diyldicarbamate and triethylamine in DMF yielding tert-butyl cis-(+/−)-1-(3-nitropyridin-4-yl)piperidine-3,5-diyldicarbamate, LCMS (m/z): 438.2 (MH⁺); LC R_t=2.95 min.

Synthesis of cis-tert-butyl (+/−)-1-(3-aminopyridin-4-yl)piperidine-3,5-diyldicarbamate

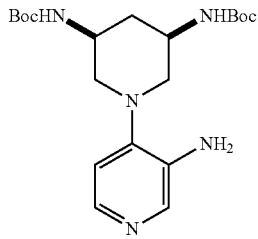 [SMILES: CC(C)(C)OC(=O)N[C@@H]1C[C@H](NC(=O)OC(C)(C)C)CN(c2ccncc2N)C1]

Following Method 1, cis-(+/−)1-(3-nitropyridin-4-yl)piperidine-3,5-diyldicarbamate in ethanol was reduced yielding cis-tert-butyl (+/−)-1-(3-aminopyridin-4-yl)piperidine-3,5-diyldicarbamate, (78%). LCMS (m/z): 408.2 (MH⁺); LC R_t=2.63 min.

Synthesis of cis (+/−)-1-benzyl 3-methyl 5-(tert-butoxycarbonylamino)-piperidine-1,3-dicarboxylate

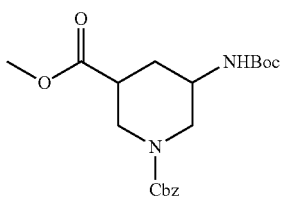 [SMILES: COC(=O)C1CC(NC(=O)OC(C)(C)C)CN(C(=O)OCc2ccccc2)C1]

To a solution of cis (+/−)-1-(benzyloxycarbonyl)-5-(tert-butoxy-carbonylamino)piperidine-3-carboxylic acid (1.0 eq), methanol (20 eq.) and EDC (1.3 eq) in dichloromethane at a concentration of 0.25 M at 0° C. was added dimethylaminopyridine (0.1 eq). After stirring for 48 hours as the reaction was allowed to warm to rt the volatiles were removed in vacuo. Upon addition of ethyl acetate and washing with H₂O (3×), 1N HCl, NaHCO₃ (sat.) and brine, the solution was dried over MgSO₄, filtered, concentrated and purified by column chromatography (25% ethyl acetate/hexanes) to yield cis (+/−)-1-benzyl 3-methyl 5-(tert-butoxycarbonylamino)-piperidine-1,3-dicarboxylate. LCMS (m/z): 293.1 (MH-Boc⁺); LC R_t=4.09 min Synthesis of cis (+/−)-benzyl 3-(tert-butoxycarbonylamino)-5-(hydroxymethyl)-piperidine-1-carboxylate

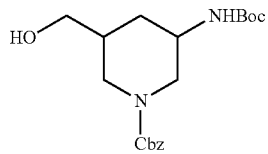 [SMILES: CC(C)(C)OC(=O)NC1CC(CO)CN(C(=O)OCc2ccccc2)C1]

A solution of cis (+/−)-1-benzyl 3-methyl 5-(tert-butoxycarbonylamino)piperidine-1,3-dicarboxylate (1.0 eq.) in THF at a concentration of 0.08 M was cooled at 0*C and then LiCl (2.3 eq.) and sodium borohydride (2.3 eq.) were added. After stirring for 20 hours as the reaction warmed to rt, the pH was adjusted with 1M citric acid to pH 4-5. After removal of the volatiles in vacuo, the product was extracted in dichloromethane, washed with H₂O and brine, dried over MgSO₄.

Upon filtering and removal of the volatiles in vacuo, cis (+/−)-benzyl 3-(tert-butoxy-carbonylamino)-5-(hydroxymethyl)piperidine-1-carboxylate was obtained as a white foamy solid. LCMS (m/z): 265.0 (MH-Boc⁺); LC R_t=3.37 min.

Synthesis of cis (+/−)-benzyl 3-(tert-butoxycarbonylamino)-5-((tert-butyldimethylsilyloxy)methyl)piperidine-1-carboxylate

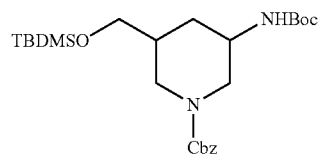 [SMILES: CC(C)(C)OC(=O)NC1CC(CO[Si](C)(C)C(C)(C)C)CN(C(=O)OCc2ccccc2)C1]

A solution of cis (+/−)-benzyl 3-(tert-butoxycarbonylamino)-5-(hydroxymethyl)piperidine-1-carboxylate (1.0 eq.), imidazole (1.1 eq.), tert-butyldimethylsilylchloride (1.1 eq.) and dimethylaminopyridine (0.1 eq.) in dichloromethane at a concentration of 0.1 M was stirred for 18 hours at which time the volatiles were removed in vacuo. Direct purification of the crude material by column chromatography (20% ethyl acetate/hexanes) yielded cis (+/−)-benzyl 3-(tert-butoxycarbonylamino)-5-((tert-butyldimethylsilyloxy)methyl)piperidine-1-carboxylate. LCMS (m/z): 379.0 (MH-Boc⁺); LC R_t=5.95 min.

Synthesis of cis (+/−)-tert-butyl 5-((tert-butyldimethylsilyloxy)-methyl)-piperidin-3-ylcarbamate

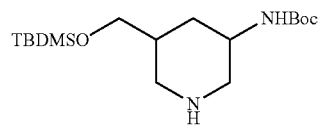 [SMILES: CC(C)(C)OC(=O)NC1CNCC(CO[Si](C)(C)C(C)(C)C)C1]

Method 1 was followed to deprotect cis (+/−)-benzyl 3-(tert-butoxycarbonylamino)-5-((tert-butyldimethylsilyloxy)methyl)piperidine-1-carboxylate yielding cis (+/−)-tert-butyl 5-((tert-butyldimethylsilyloxy)methyl)piperidin-3-ylcarbamate. LCMS (m/z): 344.1 (MH⁺).

Synthesis of cis (+/−)-tert-butyl 5-((tert-butyldimethylsilyloxy)methyl)-1-(3-nitropyridin-4-yl)piperidin-3-ylcarbamate

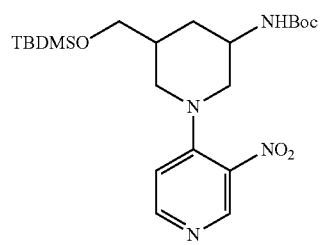 [SMILES: CC(C)(C)OC(=O)NC1CC(CO[Si](C)(C)C(C)(C)C)CN(c2ccncc2[N+](=O)[O-])C1]

Method 1 was followed using cis (+/−)-tert-butyl 5-((tert-butyldimethylsilyloxy)methyl)piperidin-3-ylcarbamate and 4-chloro-3-nitropydidine yielding cis (+/−)-tert-butyl 5-((tert-butyldimethylsilyloxy)methyl)-1-(3-nitropyridin-4-yl)piperidin-3-ylcarbamate. LCMS (m/z): 467.0 (MH+); LC R$_t$=4.02 min.

Synthesis of cis (+/−)-tert-butyl 1-(3-aminopyridin-4-yl)-5-((tert-butyldimethylsilyloxy)-methyl)piperidin-3-ylcarbamate

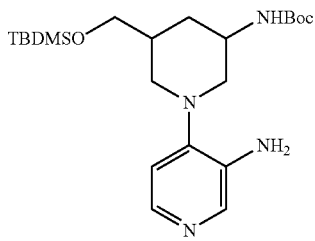 [SMILES: CC(C)(C)OC(=O)NC1CC(CO[Si](C)(C)C(C)(C)C)CN(c2ccncc2N)C1]

Following Method 1, cis (+/−)-tert-butyl 5-((tert-butyldimethylsilyloxy)methyl)-1-(3-nitropyridin-4-yl)piperidin-3-ylcarbamate was reduced yielding cis (+/−)-tert-butyl 1-(3-aminopyridin-4-yl)-5-((tert-butyldimethylsilyl-oxy)methyl)piperidin-3-ylcarbamate. LCMS (m/z): 437.2 (MH+); LC R$_t$=3.86 min.

Synthesis of cis (+/−)-benzyl 3-(tert-butoxycarbonylamino)-5-(fluoromethyl)piperidine-1-carboxylate

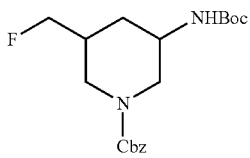 [SMILES: CC(C)(C)OC(=O)NC1CC(CF)CN(C(=O)OCc2ccccc2)C1]

A solution of cis (+/−)-benzyl 3-(tert-butoxycarbonylamino)-5-(hydroxymethyl)piperidine-1-carboxylate (1 eq.), perfluorobutanesulfonylfluoride (2 eq.), triethylamine-HF (4 eq.) and triethylamine (6 eq.) in tetrahydrofuran at a concentration of 0.16 M was stirred for 36 hours. Upon dilution with ethyl acetate (50×) the solution was washed with 1N HCl, NaHCO$_3$ $_{(sat.)}$ and brine, was dried over MgSO$_4$, filtered, concentrated and purified by column chromatography (25-40% ethyl acetate/hexanes) to yield cis (+/−)-benzyl 3-(tert-butoxycarbonylamino)-5-(fluoro-methyl)piperidine-1-carboxylate (45% yield). LCMS (m/z): 267.1 (MH+); LC R$_t$=4.23 min.

Synthesis of cis (+/−)-tert-butyl 5-(fluoromethyl)piperidin-3-ylcarbamate

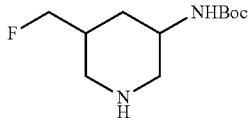

Method 1 was followed to deprotect cis (+/−)-benzyl 3-(tert-butoxycarbonylamino)-5-(fluoromethyl)piperidine-1-carboxylate yielding cis (+/−)-tert-butyl 5-(fluoromethyl)piperidin-3-ylcarbamate. LCMS (m/z): 233.1 (MH+).

Synthesis of cis (+/−)-tert-butyl 5-(fluoromethyl)-1-(3-nitropyridin-4-yl)piperidin-3-ylcarbamate

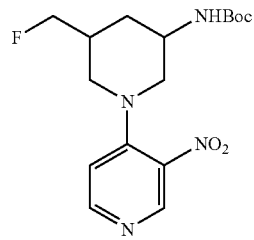

Method 1 was followed using cis (+/−)-tert-butyl 5-(fluoromethyl)piperidin-3-ylcarbamate and 4-chloro-3-nitropyridine yielding cis (+/−)-tert-butyl 5-(fluoromethyl)-1-(3-nitropyridin-4-yl)piperidin-3-ylcarbamate. LCMS (m/z): 355.1 (MH+); LC R$_t$=2.41 min.

Synthesis of cis (+/−)-tert-butyl 1-(3-aminopyridin-4-yl)-5-(fluoromethyl)piperidin-3-ylcarbamate

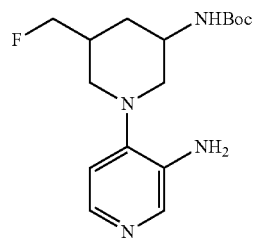

Following Method 1, cis (+/−)-tert-butyl 5-(fluoromethyl)-1-(3-nitropyridin-4-yl)piperidin-3-ylcarbamate was reduced yielding cis (+/−)-tert-butyl 1-(3-aminopyridin-4-yl)-5-(fluoromethyl)piperidin-3-ylcarbamate. LCMS (m/z): 325.1 (MH+); LC R$_t$=2.27 min.

Synthesis of (S)-tert-butyl 1-(3-aminopyridin-4-yl)piperidin-3-ylcarbamate

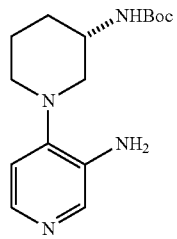 [SMILES: CC(C)(C)OC(=O)N[C@H]1CCCN(c2ccncc2N)C1]

Method 1 was followed using (S)-tert-butyl piperidin-3-ylcarbamate. LCMS (m/z): 293.1 (MH+); LC R$_t$=2.08 min.

Synthesis of (S)-tert-butyl 1-(3-aminopyridin-4-yl)pyrrolidin-3-ylcarbamate

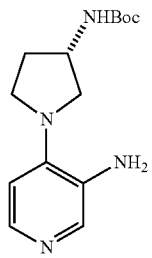 [SMILES: CC(C)(C)OC(=O)N[C@H]1CCN(c2ccncc2N)C1]

Method 1 was followed using (S)-tert-butyl pyrrolidin-3-ylcarbamate. LCMS (m/z): 279.1 (MH$^+$); LC R$_t$=1.75 min.

Synthesis of (S)-tert-butyl 1-(5-aminopyrimidin-4-yl)piperidin-3-ylcarbamate

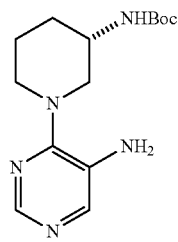

Method 1 was followed using (S)-tert-butyl piperidin-3-ylcarbamate and 2-chloro-5-nitro-4-(piperidin-1-yl)pyrimidine. LCMS (m/z): 294.2 (MH$^+$), R$_t$=0.56 min.

Synthesis of (R)-tert-butyl 1-(3-aminopyridin-4-yl)piperidin-3-ylcarbamate

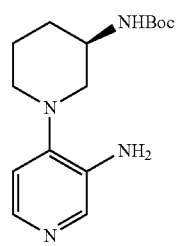 [SMILES: CC(C)(C)OC(=O)N[C@@H]1CCCN(c2ccncc2N)C1]

Method 1 was followed using (R)-tert-butyl piperidin-3-ylcarbamate. LCMS (m/z): 293.1 (MH$^+$); LC R$_t$=2.08 min.

Synthesis of tert-butyl 5-methylpyridin-3-ylcarbamate

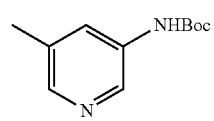

To a solution of 5-methylpyridin-3-amine (5 g, 46 mmol) in THF (80 mL) at r.t. was added 1M sodium bis(trimethylsilyl-amide) in THF (101 mL, 101 mmol), stirred for 15 min, followed by di-tert-butyldicarbonate (11 g, 49 mmol) in THF (20 mL). The reaction was stirred at r.t overnight and concentrated. The concentrate was treated with 0.2M HCl (60 mL) and EtOAc, and the organic layer was extracted, washed with NaHCO$_3$ $_{(sat.)}$ and brine, dried over Na$_2$SO$_4$, filtered and concentrated. The concentrate was purified using flash chromatography on silica gel (40% EtOAc:Hexane) to give a yellow solid as product tert-butyl 5-methylpyridin-3-ylcarbamate (8.5 g, 88% yield). LCMS (m/z): 209.1 (MH$^+$); LC R$_t$=1.94 min. $^1$H NMR (CDCl$_3$) δ 8.20 (d, 1H), 8.12 (s, 1H), 7.86 (s, 1H), 6.53 (s, 1H), 2.33 (s, 3H), 1.53 (s, 9H).

Synthesis of cis-(+/−)-tert-butyl 5-methylpiperidin-3-ylcarbamate

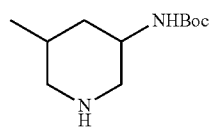

To a solution of 5-methylpyridin-3-ylcarbamate (3 g, 14 mmol) in glacial acetic Acid (50 mL) was added 5% Rhodium on active carbon (0.5 g) and Platinum(IV) oxide (0.5 g) in the hydrogenation steel bomb. The mixture was sealed and hydrogenated at 200 psi and 70° C. for 48 h. the mixture was filtered through Celite and concentrated to give cis-(+/−)-tert-butyl 5-methylpiperidin-3-ylcarbamate. LCMS (m/z): 215.1 (MH$^+$).

Synthesis of cis-(+/−)-tert-butyl 5-methyl-1-(3-nitropyridin-4-yl)piperidin-3-ylcarbamate

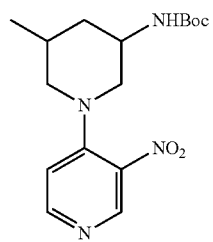 [SMILES: CC1CC(NC(=O)OC(C)(C)C)CN(c2ccncc2[N+](=O)[O-])C1]

Method 1 was followed using crude cis-(+/−)-tert-butyl 5-methylpiperidin-3-ylcarbamate yielding cis-(+/−)-tert-butyl 5-methyl-1-(3-nitropyridin-4-yl)piperidin-3-ylcarbamate (66% yield). LCMS (m/z): 337.1 (MH$^+$); LC R$_t$=2.50 min. $^1$H NMR (CDCl$_3$) δ 8.84 (s, 1H), 8.36 (d, 1H), 7.04 (m, 1H), 4.44 (m, 1H), 3.90 (m, 1H), 3.71 (m, 1H), 3.09 (d, 1H), 2.66 (q, 2H), 2.10 (d, 1H), 1.84 (m, 1H), 1.56 (s, 9H), 0.93 (d, 3H).

Synthesis of cis-(+/−)-tert-butyl 1-(3-aminopyridin-4-yl)-5-methylpiperidin-3-ylcarbamate

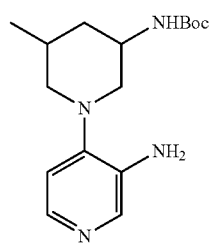 [SMILES: CC1CC(NC(=O)OC(C)(C)C)CN(c2ccncc2N)C1]

Method 1 was followed using cis-(+/−)-tert-butyl 5-methyl-1-(3-nitropyridin-4-yl)piperidin-3-ylcarbamate yielding cis-(+/−)-tert-butyl 5-methyl-1-(3-aminopyridin-4-yl)piperidin-3-ylcarbamate (98% yield). LCMS (m/z): 307.1

(MH+); LC R$_t$=2.44 min. $^1$H NMR (CDCl$_3$) δ 8.01 (s, 1H), 7.95 (d, 1H), 6.76 (d, 1H), 4.40 (m, 1H), 3.70 (m, 3H), 3.58 (dq, 1H), 3.21 (dq, 1H), 2.15 (m, 3H), 1.90 (m, 1H), 1.58 (s, 9H), 0.97 (d, 3H). 3.83 (m, 1H), 3.72 (s, 2H), 3.62 (m, 1H), 3.49 (m, 1H), 2.59 (m, 2H), 2.36 (m, 1H), 2.23 (t, 1H), 1.58 (s, 9H).

Synthesis of tert-butyl (3S,5R)-5-(tert-butyldimethylsilyloxy)piperidin-3-ylcarbamate

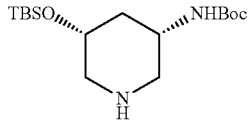

tert-Butyl (3 S,5R)-5-(tert-butyldimethylsilyloxy)piperidin-3-yl-carbamate was prepared according to the patent procedure as described by Y, Zhou; WO2005028467.

Synthesis of tert-butyl (3S,5R)-5-(tert-butyldimethylsilyloxy)-1-(3-nitropyridin-4-yl)piperidin-3-ylcarbamate

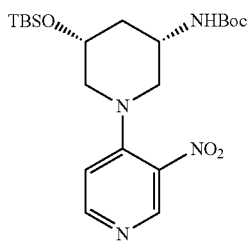 [SMILES: CC(C)(C)OC(=O)N[C@H]1C[C@@H](O[Si](C)(C)C(C)(C)C)CN(c2ccncc2[N+](=O)[O-])C1]

Method 1 was followed was followed using tert-Butyl (3S,5R)-5-(tert-butyldimethylsilyloxy)piperidin-3-ylcarbamate, yielding tert-butyl (3S,5R)-5-(tert-butyl-dimethylsilyloxy)-1-(3-nitropyridin-4-yl)piperidin-3-ylcarbamate. LC/MS (m/z): 453.2 (MH+)

Synthesis of tert-butyl (3S,5R)-1-(3-aminopyridin-4-yl)-5-(tert-butyldimethylsilyloxy)piperidin-3-ylcarbamate

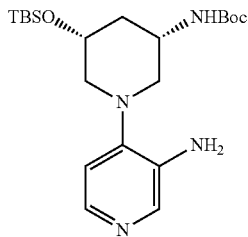 [SMILES: CC(C)(C)OC(=O)N[C@H]1C[C@@H](O[Si](C)(C)C(C)(C)C)CN(c2ccncc2N)C1]

Method 1 was followed using tert-butyl (3S,5R)-5-(tert-butyl-dimethylsilyloxy)-1-(3-nitropyridin-4-yl)piperidin-3-ylcarbamate, yielding tert-butyl (3S,5R)-1-(3-aminopyridin-4-yl)-5-(tert-butyldimethylsilyloxy)piperidin-3-ylcarbamate. LC/MS (m/z): 423.2 (MH+).

Synthesis of (3R,5R)-5-(tert-butyldimethylsilyloxy) piperidin-3-ol

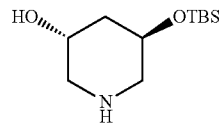 [SMILES: CC(C)(C)[Si](C)(C)O[C@H]1CNC[C@H](O)C1]

(3R,5R)-5-(tert-butyldimethylsilyloxy)piperidin-3-ol was prepared according to the patent procedure as described by Zhou, Y. WO2005028467.

Synthesis of (3R,5R)-benzyl 3-(tert-butyldimethylsilyloxy)-5-hydroxypiperidine-1-carboxylate

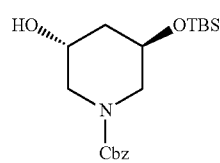 [SMILES: CC(C)(C)[Si](C)(C)O[C@@H]1C[C@@H](O)CN(C(=O)OCc2ccccc2)C1]

To a solution of (3R,5R)-5-(tert-butyldimethylsilyloxy)piperidin-3-ol (1 eq) in 20 mL of 1,4-dioxane and 8 mL of water was added benzyl chloro formate (1.5 eq). The mixture was stirred at room temperature for 4 hours. The crude mixture was diluted with 100 mL of EtOAc, washed with brine, then dried over anhydrous MgSO$_4$, filtered, and concentrated in vacuo. The crude residue was purified by flash chromatography (EtOAc:hexanes=1:3) to yield (3R,5R)-benzyl 3-(tert-butyldimethylsilyloxy)-5-hydroxypiperidine-1-carboxylate (74%). LC/MS (m/z): 366.2 (MH+).

Synthesis of (3R,5R)-benzyl 3-(tert-butyldimethylsilyloxy)-5-methoxypiperidine-1-carboxylate

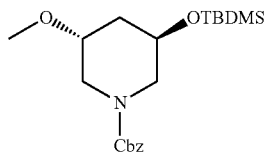 [SMILES: CO[C@@H]1C[C@@H](O[Si](C)(C)C(C)(C)C)CN(C(=O)OCc2ccccc2)C1]

To a solution of (3R,5R)-benzyl 3-(tert-butyldimethylsilyloxy)-5-hydroxypiperidine-1-carboxylate (1 eq) in 30 mL of THF was added sodium hydride (1.5 eq) and followed by methyl iodide (5 eq) at 0° C. The reaction mixture was allowed to stir at room temperature for 3 hours. The crude mixture was diluted with 120 mL of EtOAc, washed with brine, then dried over anhydrous MgSO$_4$, filtered, and concentrated in vacuo. The crude residue was purified by flash chromatography (EtOAc:hexanes=1:5) to yield (3R,5R)- benzyl 3-(tert-butyldimethylsilyloxy)-5-methoxypiperidine-1-carboxylate (93%). LC/MS (m/z): 380.2 (MH+).

Synthesis of (3R,5R)-benzyl 3-hydroxy-5-methoxypiperidine-1-carboxylate

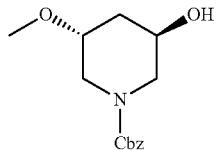 [SMILES: CO[C@@H]1C[C@@H](O)CN(C(=O)OCc2ccccc2)C1]

To a solution of (3R,5R)-benzyl 3-(tert-butyldimethylsilyloxy)-5-methoxypiperidine-1-carboxylate (1 eq) in 30 mL of methanol was added 3.8M HCl in isopropanol (4 eq). The reaction mixture was allowed to stand at room temperature for 3 hours at which point it was concentrated under reduced pressure. The resulting residue was diluted with 100 mL of EtOAc, washed with sat. aq. sodium bicarbonate, brine, then dried over anhydrous MgSO$_4$, filtered, and concentrated in vacuo. The crude residue was purified by flash chromatography (EtOAc:hexanes=2:1) to yield (3R,5R)-benzyl 3-hydroxy-5-methoxypiperidine-1-carboxylate (92%). LC/MS (m/z): 266.2 (MH+).

Synthesis of (3S,5R)-benzyl 3-azido-5-methoxypiperidine-1-carboxylate

To a solution of (3R,5R)-benzyl 3-hydroxy-5-methoxypiperidine-1-carboxylate (1 eq) in 40 mL of dichloromethane was added triethyl amine (3 eq) and methanesulfonyl chloride (1.5 eq) at 0° C. The reaction mixture was allowed to stir at room temperature for 2 hours. The crude mixture was diluted with 150 mL of EtOAc, washed with sat. aq. sodium bicarbonate, brine, then dried over anhydrous MgSO$_4$, filtered, and concentrated in vacuo. The crude residue was purified by flash chromatography (EtOAc:hexanes=1:1) to give the intermediate, which was dissolved in 15 mL of DMF. Sodium azide (3.3 eq) was added and the resulting suspension was stirred at 80° C. overnight. The reaction mixture was diluted with 150 mL of EtOAc, washed with water, brine, then dried over anhydrous MgSO$_4$, filtered, and concentrated in vacuo. The crude residue was purified by flash chromatography (EtOAc:hexanes=1:2) to yield (3S,5R)-benzyl 3-azido-5-methoxypiperidine-1-carboxylate_(95%). LC/MS (m/z): 263.2 (MH+-28).

Synthesis of (3S,5R)-benzyl 3-(tert-butoxycarbonylamino)-5-methoxypiperidine-1-carboxylate

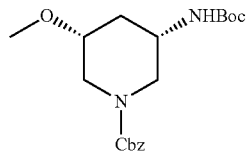 [SMILES: CO[C@@H]1C[C@H](NC(=O)OC(C)(C)C)CN(C(=O)OCc2ccccc2)C1]

To a solution of (3S,5R)-benzyl 3-azido-5-methoxypiperidine-1-carboxylate (1 eq) in a mixture of 14 mL of pyridine and 2 mL of ammonium hydroxide was added 1M trimethylphosphine (3 eq) at room temperature. The reaction mixture was stirred at room temperature for 4 hours at which point the solvents were removed under reduced pressure to give a yellow oil. The oil was again dissolved in 100 mL of ethanol and concentrated to remove ammonium hydroxide completely. The residue was dissolved in 16 ml of 1,4-dioxane and 16 mL of sat. aq. NaHCO$_3$ was added. Di-tert-butyl dicarbonate (4 eq) in 8 mL of THF was added dropwise at 0° C. The mixture was allowed to stir at room temperature for 2 hours. The crude mixture was diluted with 300 mL of EtOAc, washed with brine, then dried over anhydrous MgSO$_4$, filtered, and concentrated in vacuo. The crude residue was purified by flash chromatography (EtOAc:hexanes=1:1) to yield (3S,5R)-benzyl 3-(tert-butoxycarbonylamino)-5-methoxypiperidine-1-carboxylate (86%). LC/MS (m/z): 365.0 (MH+).

Synthesis of tert-butyl (3S,5R)-5-methoxy-1-(3-nitropyridin-4-yl)piperidin-3-ylcarbamate

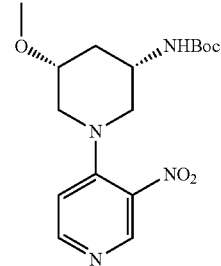 [SMILES: CO[C@@H]1C[C@H](NC(=O)OC(C)(C)C)CN(c2ccncc2[N+](=O)[O-])C1]

To a solution of (3S,5R)-benzyl 3-(tert-butoxycarbonylamino)-5-methoxypiperidine-1-carboxylate (1 eq) in 25 methanol was added 10% Pd/C (0.1 eq). The resulting suspension was stirred at H$_2$ atmosphere for 2 hours. The crude solids were filtered through a pad of Celite on a paper lined Buchner funnel, washed with MeOH, then concentrated in vacuo. The residue was dissolved in 25 mL of isopropanol and DIEA (1.8 eq) and 4-chloro-3-nitropyridine (1.2 eq) were added. The reaction mixture was stirred at 80° C. for 4 hours, at which point the reaction mixture was allowed to cool to room temperature and concentrated under reduced pressure. The residue was diluted with 150 mL of EtOAc, washed with brine, then dried over anhydrous MgSO$_4$, filtered, and concentrated in vacuo. The crude residue was purified by flash chromatography (5% methanol in EtOAc:hexanes=1:1) to yield (3S,5R)-5-methoxy-1-(3-nitropyridin-4-yl)piperidin-3-ylcarbamate (88%). LC/MS (m/z): 353.0 (MH⁺). HPLC: R$_t$:2.15 min.

Synthesis of tert-Butyl (3S,5R)-1-(3-aminopyridin-4-yl)-5-methoxypiperidin-3-ylcarbamate

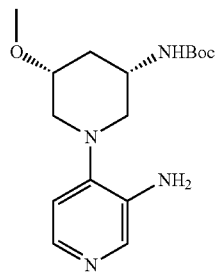 [SMILES: CO[C@@H]1C[C@H](NC(=O)OC(C)(C)C)CN(c2ccncc2N)C1]

Following Method 1, tert-butyl (3S,5R)-5-methoxy-1-(3-nitropyridin-4-yl)piperidin-3-ylcarbamate was reduced yielding tert-Butyl (3S,5R)-1-(3-aminopyridin-4-yl)-5-methoxypiperidin-3-ylcarbamate. LC/MS (m/z): 323.1 (MH⁺).

Synthesis of tert-butyl (3S,5R)-1-(3-aminopyridin-4-yl)-5-ethoxypiperidin-3-ylcarbamate

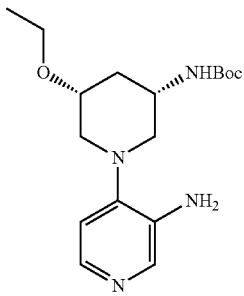 [SMILES: CCO[C@@H]1C[C@H](NC(=O)OC(C)(C)C)CN(c2ccncc2N)C1]

Method 1 was followed using (3R,5R)-benzyl 3-(tert-butyldimethyl-silylo xy)-5-hydroxypiperidine-1-carboxylate and ethyl iodide. LC/MS (m/z): 337.1 (MH⁺), Rt=0.63.

Method 2

Synthesis of 2-(2,6-difluorophenyl)-8-methoxyquinazoline

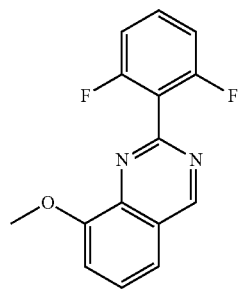 [SMILES: COc1cccc2cnc(-c3c(F)cccc3F)nc12]

2-chloro-8-methoxyquinazoline (1.0 eq), 2,6-difluorophenylboronic acid (1.5 eq), and DIPEA (3 eq) was mixed with toluene and ethanol (1:1, 0.5M) in a microwave vial. The reaction mixture was degassed by anhydrous N$_2$ stream for 5 min followed by the addition of Pd(dppf)Cl$_2$-DCM (0.1 eq). The reaction mixture was stirred at 130° C. for 30 min in microwave. Solvents were removed under reduced pressure. The crude product was purified by column (ethyl acetate:hexanes=1:1) to give the mixture of starting material chloride and desired product. The mixture was treated with 1N HCl in 1,4-dioxane. Solvents were removed under reduced pressure. The residue was dissolved in ethyl acetate (150 mL), and washed with NaHCO$_3$, brine, then dried over MgSO$_4$, filtered, and evaporated under reduced pressure to give crude product, which was purified by column (ethyl acetate:hexanes=1:1) to yield 2-(2,6-difluorophenyl)-8-methoxyquinazoline (46%). LC/MS (m/z): 273.0 (MH⁺), Rt=0.78.

Synthesis of 2-(2,6-difluorophenyl)quinazolin-8-ol

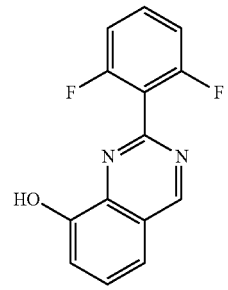 [SMILES: Oc1cccc2cnc(-c3c(F)cccc3F)nc12]

To a solution of the 2-(2,6-difluorophenyl)-8-methoxyquinazoline (1.0 eq) in methylene chloride (0.23M) was added BBr$_3$ (2.0 eq) at room temperature. The reaction mixture was stirred overnight. The solvents were removed under reduced pressure. The residue was dissolved in ethyl acetate (150 mL), and washed with NaHCO$_3$, brine, then dried over MgSO$_4$, filtered, and evaporated under reduced pressure to give crude product, which was purified by column (ethyl acetate:hexanes=1:2) to yield 2-(2,6-difluorophenyl)quinazolin-8-ol (94%). LC/MS (m/z): 259.0 (MH⁺), Rt=0.82.

Synthesis of 2-(2,6-difluorophenyl)quinazolin-8-yl trifluoromethanesulfonate

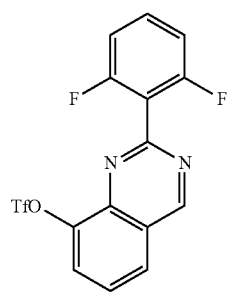 [SMILES: O=S(=O)(Oc1cccc2cnc(-c3c(F)cccc3F)nc12)C(F)(F)F]

To a solution of the 2-(2,6-difluorophenyl)quinazolin-8-ol (1.0 eq) in methylene chloride (0.17M) was added DIPEA (2.0 eq) and 1,1,1-trifluoro-N-phenyl-N-(trifluoromethylsulfonyl)methanesulfonamide (1.5 eq) at room temperature. The reaction mixture was stirred overnight. The solvents were removed under reduced pressure. The residue was dissolved in ethyl acetate (120 mL), and washed with water, brine, then dried over MgSO$_4$, filtered, and evaporated under reduced pressure to give crude product, which was purified by column (ethyl acetate:hexanes=1:1) to yield 2-(2,6-difluorophenyl)quinazolin-8-yl trifluoromethanesulfonate (73%). LC/MS (m/z): 391.0 (MH⁺), Rt=1.08.

Synthesis of 2-(8-methoxyquinazolin-2-yl)thiazole

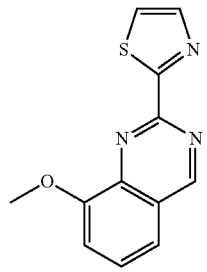 [SMILES: COc1cccc2cnc(-c3nccs3)nc12]

2-Chloro-8-methoxyquinazoline (1.0 eq), and thiazol-2-ylzinc(II) bromide (1M in THF, 3 eq) was degassed by anhydrous N$_2$ stream for 5 min followed by the addition of Pd(dppf)Cl$_2$-DCM (0.1 eq). The reaction mixture was stirred at 50° C. for 1 hour. Solvents were removed under reduced pressure. The crude product was purified by column (10% methanol in ethyl acetate:hexanes=1:1) to give 2-(8-methoxyquinazolin-2-yl)thiazole (20%). LC/MS (m/z): 243.9 (MH⁺), Rt=0.68.

Synthesis of 2-(thiazol-2-yl)quinazolin-8-yl trifluoromethanesulfonate

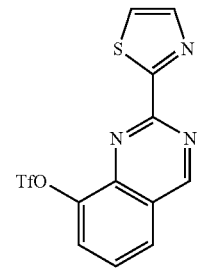 [SMILES: O=S(=O)(Oc1cccc2cnc(-c3nccs3)nc12)C(F)(F)F]

Method 2 was followed using 2-(8-methoxyquinazolin-2-yl)thiazole. LC/MS (m/z): 361.8 (MH⁺), Rt=0.90.

Synthesis of 2-(2-fluorophenyl)quinazolin-8-yl trifluoromethanesulfonate

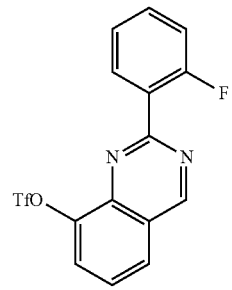 [SMILES: O=S(=O)(Oc1cccc2cnc(-c3ccccc3F)nc12)C(F)(F)F]

Method 2 was followed using 2-fluorophenylboronic acid. LC/MS (m/z): 373.0 (MH⁺), Rt=1.12.

Method 3

Example 15

Synthesis of N-(4-((3S,5R)-3-amino-5-methylpiperidin-1-yl)pyridin-3-yl)-2-(2,6-difluorophenyl)quinazolin-8-amine

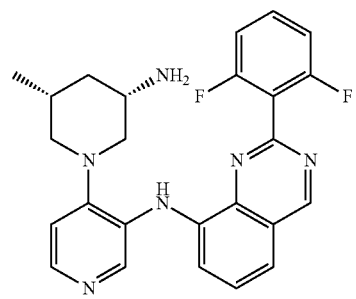 [SMILES: C[C@@H]1C[C@H](N)CN(c2ccncc2Nc2cccc3cnc(-c4c(F)cccc4F)nc23)C1]

To a solution of the tert-butyl (3S,5R)-1-(3-aminopyridin-4-yl)-5-methylpiperidin-3-ylcarbamate (1.0 eq) in 1,4-dioxane (0.067M) was added 2-(2,6-difluorophenyl)quinazolin-8-yl trifluoromethanesulfonate (1.0 eq), palladium acetate (0.2 eq), BINAP (1.5 eq), and cesium carbonate (3.0 eq). The reaction mixture was stirred at 120° C. for 10 min in microwave. The residue was dissolved in ethyl acetate (120 mL), and washed with water, brine, then dried over MgSO$_4$, filtered, and evaporated under reduced pressure to give crude product, which was purified by column (ethyl acetate:hexanes=1:1 with 10% methanol) to yield tert-butyl (3S,5R)-1-(3-(2-(2,6-difluorophenyl)-quinazolin-8-ylamino)pyridin-4-yl)-5-methylpiperidin-3-ylcarbamate (79%). LC/MS (m/z): 547.1 (MH⁺), Rt=0.87

The mixture of 2-(2,6-difluorophenyl)quinazolin-8-yl trifluoro-methanesulfonate (1.0 eq) in 20% TFA in methylene chloride (0.02M) was stirred at room temperature for 1 hour. Solvents were removed under reduced pressure. The crude product was purified by reversed HPLC to give N-(4-((3S,5R)-3-amino-5-methylpiperidin-1-yl)pyridin-3-yl)-2-(2,6-difluorophenyl)quinazolin-8-amine (96%). LC/MS (m/z): 447.1 (MH⁺), Rt=0.57. HPLC: R$_t$: 2.09 min.

If TBDMS ethers were present they were deprotected prior to Boc removal by treating with 6N HCl, THF, methanol (1:2:1) at room temperature for 2 h. After removal of volatiles in vacuo, the Boc amino group was deprotected as described above.

If an N-Boc1,2 amino alcohol cyclic carbamate was present, prior to Boc deprotection the cyclic carbamate could be cleaved by treating with Cs$_2$CO$_3$ (0.5 eq) in methanol at a concentration of 0.1 M for three hours. After removal of volatiles in vacuo, the Boc amino group was deprotected as described above.

The following compounds were prepared following the procedures of Method 3.

| Ex. No | Structure | Compound Name | MH+ | LC |
|---|---|---|---|---|
| 1 | 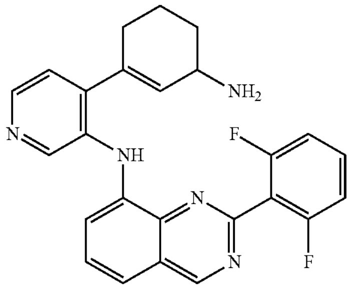 [SMILES: NC1C=C(c2ccncc2Nc2cccc3cnc(-c4c(F)cccc4F)nc23)CCC1] | N-(4-(3-aminocyclohex-1-enyl)pyridin-3-yl)-2-(2,6-difluorophenyl)quinazolin-8-amine | 430.2 | 2.01 |
| 2 | 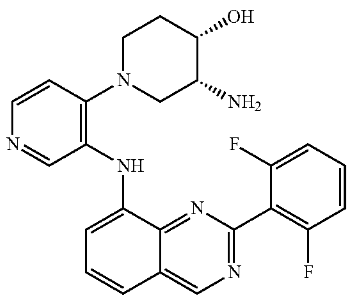 [SMILES: N[C@@H]1CN(c2ccncc2Nc2cccc3cnc(-c4c(F)cccc4F)nc23)CC[C@@H]1O] | (3R,4S)-3-amino-1-(3-(2-(2,6-difluorophenyl)-quinazolin-8-ylamino)-pyridin-4-yl)piperidin-4-ol | 449.1 | 1.85 |
| 3 | 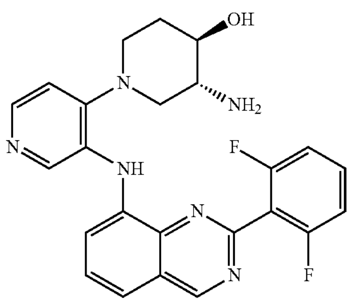 [SMILES: N[C@@H]1CN(c2ccncc2Nc2cccc3cnc(-c4c(F)cccc4F)nc23)CC[C@H]1O] | (3R,4R)-3-amino-1-(3-(2-(2,6-difluorophenyl)-quinazolin-8-ylamino)-pyridin-4-yl)piperidin-4-ol | 449.1 | 1.83 |
| 4 | 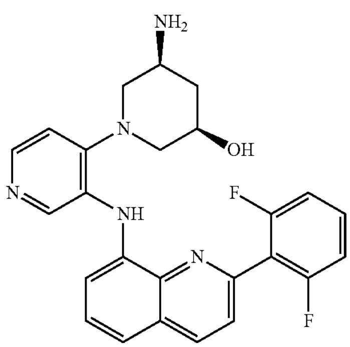 [SMILES: N[C@H]1C[C@@H](O)CN(c2ccncc2Nc2cccc3ccc(-c4c(F)cccc4F)nc23)C1] | (3R,5S)-5-amino-1-(3-(2-(2,6-difluorophenyl)quinolin-8-ylamino)pyridin-4-yl)piperidin-3-ol | 449.1 | 1.7 |
| 5 | 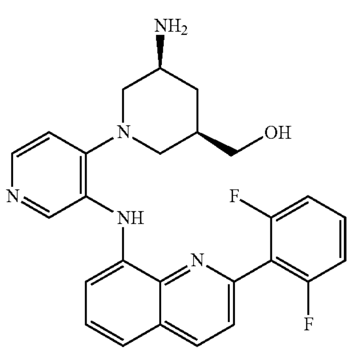 [SMILES: N[C@H]1C[C@@H](CO)CN(c2ccncc2Nc2cccc3ccc(-c4c(F)cccc4F)nc23)C1] | ((3R,5S)-5-amino-1-(3-(2-(2,6-difluorophenyl)quinolin-8-ylamino)pyridin-4-yl)piperidin-3-yl)methanol | 463.1 | 1.91 |

-continued

| Ex. No | Structure | Compound Name | MH+ | LC |
|---|---|---|---|---|
| 6 | 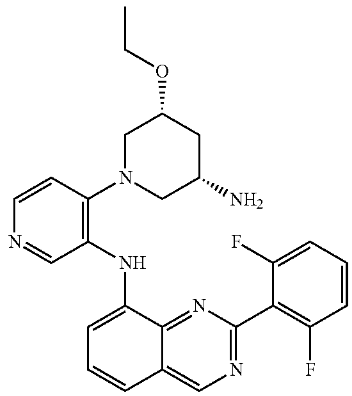 [SMILES: CCO[C@@H]1C[C@H](N)CN(c2ccncc2Nc2cccc3cnc(-c4c(F)cccc4F)nc23)C1] | N-(4-((3S,5R)-3-amino-5-ethoxypiperidin-1-yl)pyridin-3-yl)-2-(2,6-difluorophenyl)quinazolin-8-amine | 477.2 | 2.03 |
| 7 | 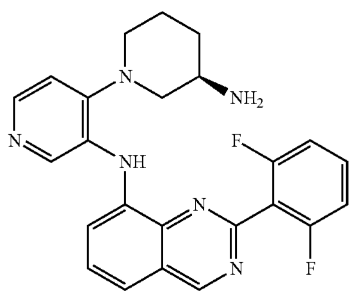 [SMILES: N[C@@H]1CCCN(c2ccncc2Nc2cccc3cnc(-c4c(F)cccc4F)nc23)C1] | (R)-N-(4-(3-aminopiperidin-1-yl)pyridin-3-yl)-2-(2,6-difluorophenyl)quinazolin-8-amine | 433.1 | 1.95 |
| 8 | 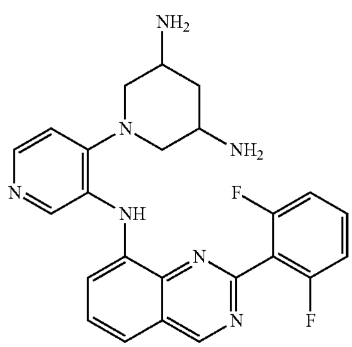 [SMILES: NC1CC(N)CN(c2ccncc2Nc2cccc3cnc(-c4c(F)cccc4F)nc23)C1] | 1-(3-(2-(2,6-difluorophenyl)quinazolin-8-ylamino)pyridin-4-yl)piperidine-3,5-diamine | 448.1 | 1.52 |
| 9 | 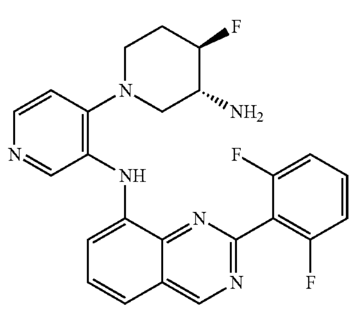 [SMILES: N[C@@H]1CN(c2ccncc2Nc2cccc3cnc(-c4c(F)cccc4F)nc23)CC[C@H]1F] | N-(4-((3R,4R)-3-amino-4-fluoropiperidin-1-yl)pyridin-3-yl)-2-(2,6-difluorophenyl)quinazolin-8-amine | 451.1 | 1.93 |

-continued

| Ex. No | Structure | Compound Name | MH+ | LC |
|---|---|---|---|---|
| 10 | 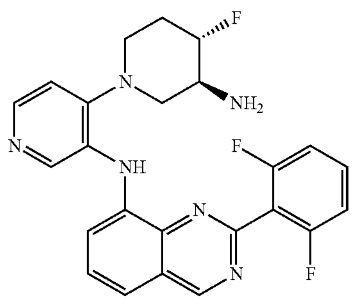 [SMILES: N[C@H]1CN(c2ccncc2Nc2cccc3cnc(-c4c(F)cccc4F)nc23)CC[C@@H]1F] | N-(4-((3S,4S)-3-amino-4-fluoropiperidin-1-yl)pyridin-3-yl)-2-(2,6-difluorophenyl)quinazolin-8-amine | 451.1 | 1.96 |
| 11 | 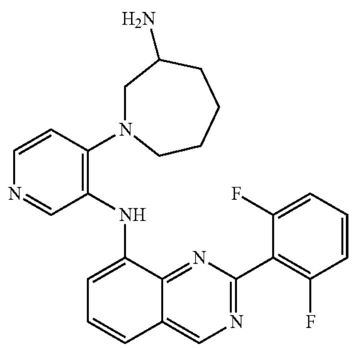 [SMILES: NC1CCCCN(c2ccncc2Nc2cccc3cnc(-c4c(F)cccc4F)nc23)C1] | N-(4-(3-aminoazepan-1-yl)pyridin-3-yl)-2-(2,6-difluorophenyl)quinazolin-8-amine | 447.2 | 1.94 |
| 12 | 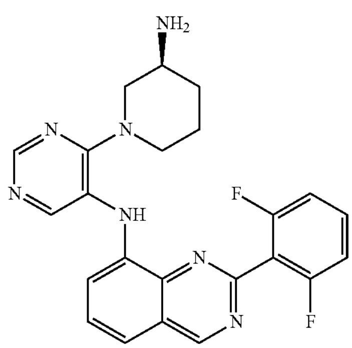 [SMILES: N[C@H]1CCCN(c2ncncc2Nc2cccc3cnc(-c4c(F)cccc4F)nc23)C1] | (S)-N-(4-(3-aminopiperidin-1-yl)pyrimidin-5-yl)-2-(2,6-difluorophenyl)quinazolin-8-amine | 434.2 | 1.9 |
| 13 | 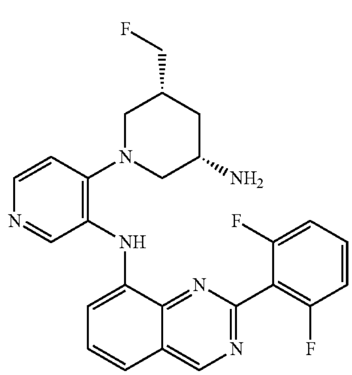 [SMILES: N[C@H]1C[C@@H](CF)CN(c2ccncc2Nc2cccc3cnc(-c4c(F)cccc4F)nc23)C1] | N-(4-((3S,5R)-3-amino-5-(fluoromethyl)piperidin-1-yl)pyridin-3-yl)-2-(2,6-difluorophenyl)quinazolin-8-amine | 465.2 | 2.04 |

| Ex. No | Structure | Compound Name | MH+ | LC |
|---|---|---|---|---|
| 14 | 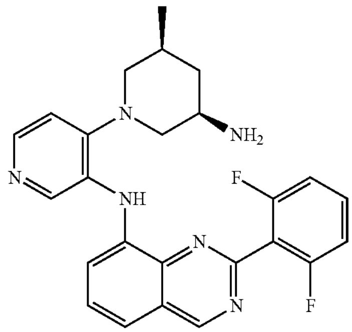 [SMILES: C[C@H]1C[C@@H](N)CN(c2ccncc2Nc2cccc3cnc(-c4c(F)cccc4F)nc23)C1] | N-(4-((3R,5S)-3-amino-5-methylpiperidin-1-yl)pyridin-3-yl)-2-(2,6-difluorophenyl)quinazolin-8-amine | 447.2 | 2.1 |
| 15 | 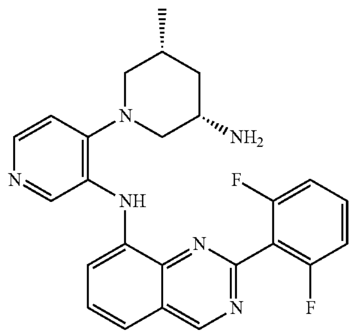 [SMILES: C[C@@H]1C[C@H](N)CN(c2ccncc2Nc2cccc3cnc(-c4c(F)cccc4F)nc23)C1] | N-(4-((3S,5R)-3-amino-5-methylpiperidin-1-yl)pyridin-3-yl)-2-(2,6-difluorophenyl)quinazolin-8-amine | 447.1 | 2.08 |
| 16 | 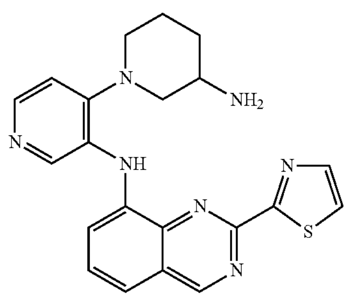 [SMILES: NC1CCCN(c2ccncc2Nc2cccc3cnc(-c4nccs4)nc23)C1] | (S)-N-(4-(3-aminopiperidin-1-yl)pyridin-3-yl)-2-(thiazol-2-yl)quinazolin-8-amine | 404 | 1.84 |
| 17 | 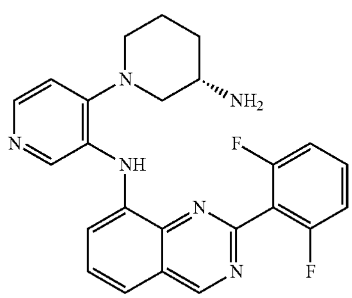 [SMILES: N[C@H]1CCCN(c2ccncc2Nc2cccc3cnc(-c4c(F)cccc4F)nc23)C1] | (S)-N-(4-(3-aminopiperidin-1-yl)pyridin-3-yl)-2-(2,6-difluorophenyl)quinazolin-8-amine | 433.1 | 1.96 |
| 18 | 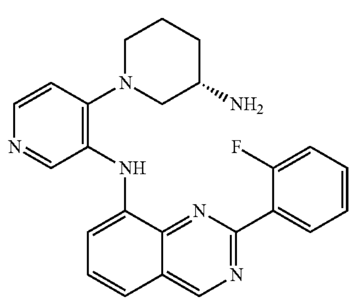 [SMILES: N[C@H]1CCCN(c2ccncc2Nc2cccc3cnc(-c4ccccc4F)nc23)C1] | (S)-N-(4-(3-aminopiperidin-1-yl)pyridin-3-yl)-2-(2-fluorophenyl)quinazolin-8-amine | 415.1 | 2.04 |

| Ex. No | Structure | Compound Name | MH+ | LC |
|---|---|---|---|---|
| 19 | 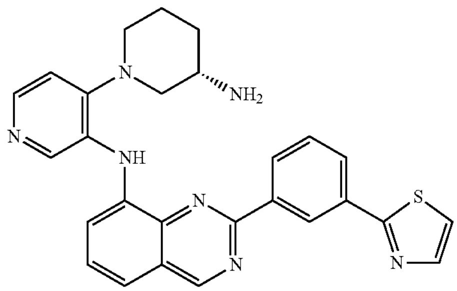 [SMILES: N[C@H]1CCCN(c2ccncc2Nc2cccc3cnc(-c4cccc(-c5nccs5)c4)nc23)C1] | (S)-N-(4-(3-aminopiperidin-1-yl)pyridin-3-yl)-2-(3-(thiazol-2-yl)phenyl)quinazolin-8-amine | | |

Example 20

Pim1 ATP Depletion Assay

The activity of PIM1 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µA per well. To start the reaction, 10 µl of 5 nM Pim1 kinase and 80 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 40 µM ATP in assay buffer is added. Final assay concentrations are 2.5 nM PIM1, 20 µM ATP, 40 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim1 ATP depletion assay and found to exhibit an $IC_{50}$ values as shown in Example 24, below. $IC_{50}$, the half maximal inhibitory concentration, represents the concentration of a test compound that is required for 50% inhibition of its target in vitro.

Example 21

Pim2 ATP Depletion Assay

The activity of PIM2 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim2 kinase and 20 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 8 µM ATP in assay buffer is added. Final assay concentrations are 5 nM PIM2, 4 µM ATP, 10 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim2 ATP depletion assay and found to exhibit an $IC_{50}$ values as shown in Example 24, below.

Example 22

Pim3 ATP Depletion Assay

The activity of PIM3 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µA per well. To start the reaction, 10 µl of 10 nM Pim3 kinase and 200 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 80 µM ATP in assay buffer is added. Final assay concentrations are 5 nM PIM1, 40 µM ATP, 100 µM BAD peptide and 2.5% DMSO. The reaction is performed until approximately 50% of the ATP is depleted, then stopped by the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim3 ATP depletion assay and found to exhibit an $IC_{50}$ values as shown in Example 24, below.

Example 23

Cell Proliferation Assay

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay. MM1.s (human myeloma cell line), were cultured in RPMI1640 supplemented with 10% FBS, sodium pyruvate and antibiotics. Cells were plated in the same medium at a density of 5000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2x compounds were added to the cells in 96 well plates and incubated at 37° C. for 3 days.

After 3 days plates were equilibrated to room temperature and equal volume of CellTiter-Glow Reagent (Promega) was added to the culture wells. The plates were agitated briefly and luminescent signal was measured with luminometer. The percent inhibition of the signal seen in cells treated with DMSO alone vs. cells treated with control compound was calculated and used to determine $EC_{50}$ values (i.e., the concentration of a test compound that is required to obtain 50% of the maximum effect in the cells) for tested compounds, as shown in Example 24.

Example 24

$IC_{50}$ and $EC_{50}$ Activity of Compounds of the Invention

Using the procedures of Examples 20 (Pim1 ATP depletion assay), 21 (Pim2 ATP depletion assay), and 22 (Pim3 ATP depletion assay), the $IC_{50}$ concentration of compounds of the previous examples were determined as shown in the following table.

Using the procedures of Example 23 (cell proliferation assay), the $EC_{50}$ concentration of compounds of the previous examples in were determined in KMS11 cells as shown in the following table.

| Ex. No | Compound Name | IC50 (μM) | | | EC50 (μM) |
|---|---|---|---|---|---|
| | | PIM1 | PIM2 | PIM3 | KMS11 |
| 1 | N-(4-(3-aminocyclohex-1-enyl)-pyridin-3-yl)-2-(2,6-difluoro-phenyl)quinazolin-8-amine | 0.152 | 0.392 | 0.078 | |
| 2 | (3R,4S)-3-amino-1-(3-(2-(2,6-difluorophenyl)quinazolin-8-ylamino)pyridin-4-yl)piperidin-4-ol | 0.039 | 0.090 | 0.018 | |
| 3 | (3R,4R)-3-amino-1-(3-(2-(2,6-difluorophenyl)quinazolin-8-ylamino)pyridin-4-yl)piperidin-4-ol | 0.184 | 0.230 | 0.067 | |
| 4 | (3R,5S)-5-amino-1-(3-(2-(2,6-difluorophenyl)quinolin-8-ylamino)pyridin-4-yl)piperidin-3-ol | 0.589 | 0.512 | 0.061 | |
| 5 | ((3R,5S)-5-amino-1-(3-(2-(2,6-difluorophenyl)quinolin-8-ylamino)pyridin-4-yl)piperidin-3-yl)methanol | 0.796 | 0.286 | 0.293 | |
| 6 | N-(4-((3S,5R)-3-amino-5-ethoxypiperidin-1-yl)pyridin-3-yl)-2-(2,6-difluorophenyl)quinazolin-8-amine | 1.7 | 0.460 | 2.1 | |
| 7 | (R)-N-(4-(3-aminopiperidin-1-yl)pyridin-3-yl)-2-(2,6-difluorophenyl)quinazolin-8-amine | 2.1 | 3.6 | 0.212 | |
| 8 | 1-(3-(2-(2,6-difluorophenyl)quinazolin-8-ylamino)pyridin-4-yl)piperidine-3,5-diamine | 2.3 | 2.5 | 0.246 | |
| 9 | N-(4-((3R,4R)-3-amino-4-fluoropiperidin-1-yl)pyridin-3-yl)-2-(2,6-difluorophenyl)quinazolin-8-amine | 0.465 | 0.498 | 0.170 | |
| 10 | N-(4-((3S,4S)-3-amino-4-fluoropiperidin-1-yl)pyridin-3-yl)-2-(2,6-difluorophenyl)quinazolin-8-amine | 4.7 | >25 | 0.502 | |
| 11 | N-(4-(3-aminoazepan-1-yl)pyridin-3-yl)-2-(2,6-difluorophenyl)quinazolin-8-amine | 2.9 | >25 | 0.468 | |
| 12 | (S)-N-(4-(3-aminopiperidin-1-yl)pyrimidin-5-yl)-2-(2,6-difluorophenyl)quinazolin-8-amine | 5.4 | >25 | 3.9 | |
| 13 | N-(4-((3S,5R)-3-amino-5-(fluoromethyl)piperidin-1-yl)pyridin-3-yl)-2-(2,6-difluorophenyl)quinazolin-8-amine | 0.053 | 0.020 | 0.049 | 7.3 |
| 14 | N-(4-((3R,5S)-3-amino-5-methylpiperidin-1-yl)pyridin-3-yl)-2-(2,6-difluorophenyl)quinazolin-8-amine | 0.882 | 0.852 | 0.180 | |
| 15 | N-(4-((3S,5R)-3-amino-5-methylpiperidin-1-yl)pyridin-3-yl)-2-(2,6-difluorophenyl)quinazolin-8-amine | 0.018 | 0.009 | 0.019 | 2.6 |
| 16 | (S)-N-(4-(3-aminopiperidin-1-yl)pyridin-3-yl)-2-(thiazol-2-yl)quinazolin-8-amine | 0.411 | 1.9 | 0.149 | |
| 17 | (S)-N-(4-(3-aminopiperidin-1-yl)pyridin-3-yl)-2-(2,6-difluorophenyl)quinazolin-8-amine | 0.021 | 0.031 | 0.016 | |
| 18 | (S)-N-(4-(3-aminopiperidin-1-yl)pyridin-3-yl)-2-(2-fluorophenyl)quinazolin-8-amine | 0.029 | 0.131 | 0.018 | |
| 19 | (S)-N-(4-(3-aminopiperidin-1-yl)pyridin-3-yl)-2-(3-(thiazol-2-yl)phenyl)quinazolin-8-amine | 0.056 | 2 | 0.095 | |

While illustrative embodiments have been illustrated and described, it will be appreciated that various changes can be made therein without departing from the spirit and scope of the invention.

The invention claimed is:

1. A compound of Formula II:

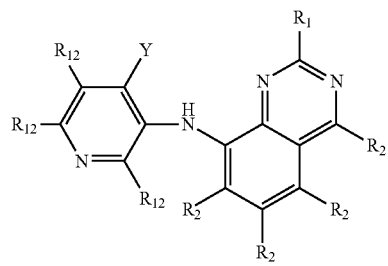

or a stereoisomer, tautomer, or pharmaceutically acceptable salt thereof, wherein:

Y is selected from piperidinyl, cyclohexyl, and partially unsaturated cyclohexyl, wherein each member of said group is substituted with up to 4 substituents selected from hydrogen, amino, halo, hydroxyl, hydroxyl alkyl, methoxy, ethoxy, monofluoro methyl, difluoro methyl, and trifluoro methyl;

$R_1$ is selected from a group consisting of aryl, heteroaryl, cycloalkyl, heterocycloalkyl, wherein each member of said group is substituted with up to 4 substituents selected from hydrogen, halogen, alkyl, amino, hydroxyl, alkoxy, and cyano; and $R_2$ and $R_{12}$ independently at each occurrence are selected from the group consisting of hydrogen, halo, hydroxyl, amino, cyano, $C_{1-4}$ alkoxy and $C_{1-4}$ alkyl.

2. A compound of claim 1, wherein:

Y is selected from a group consisting of piperidinyl, cyclohexyl, and partially unsaturated cyclohexyl, wherein each of member of said group is substituted with up to 4 substituents selected from hydrogen, amino, halo, hydroxyl, hydroxyl alkyl, methoxy, ethoxy, monofluoro methyl, difluoro methyl, and trifluoro methyl; and $R_1$ is selected from aryl and heteroaryl, wherein each member of said group is substituted with up to 4 substituents selected from hydrogen, halogen, alkyl, amino, hydroxyl, alkoxy, and cyano.

3. A compound of claim 2 selected from the group consisting of N-(4-(3-aminocyclohex-1-enyl)pyridin-3-yl)-2-(2,6-difluorophenyl)quinazolin-8-amine, (3R,4S)-3-amino-1-(3-(2-(2,6-difluorophenyl)quinazolin-8-ylamino)pyridin-4-yl)-piperidin-4-ol, (3R,4R)-3-amino-1-(3-(2-(2,6-difluorophenyl)quinazolin-8-ylamino)pyridin-4-yl)piperidin-4-ol, (3R,5S)-5-amino-1-(3-(2-(2,6-difluorophenyl)quinolin-8-ylamino)pyridin-4-yl)piperidin-3-ol, ((3R,5S)-5-amino-1-(3-(2-(2,6-difluorophenyl)quinolin-8-ylamino)pyridin-4-yl)piperidin-3-yl)methanol, N-(4-((3S,5R)-3-amino-5-ethoxypiperidin-1-yl)pyridin-3-yl)-2-(2,6-difluorophenyl)quinazolin-8-amine, (R)—N-(4-(3-aminopiperidin-1-yl)pyridin-3-yl)-2-(2,6-difluorophenyl)quinazolin-8-amine, 1-(3-(2-(2,6-difluorophenyl)quinazolin-8-ylamino)pyridin-4-yl)piperidine-3,5-diamine, N-(4-((3R,4R)-3-amino-4-fluoropiperidin-1-yl)pyridin-3-yl)-2-(2,6-difluorophenyl)quinazolin-8-amine, N-(4-((3S,4S)-3-amino-4-fluoropiperidin-1-yl)pyridin-3-yl)-2-(2,6-difluorophenyl)quinazolin-8-amine, N-(4-(3-aminoazepan-1-yl)pyridin-3-yl)-2-(2,6-difluorophenyl)quinazolin-8-amine, (S)—N-(4-(3-aminopiperidin-1-yl)pyrimidin-5-yl)-2-(2,6-difluorophenyl)quinazolin-8-amine, N-(4-((3S,5R)-3-amino-5-(fluoromethyl)piperidin-1-yl)pyridin-3-yl)-2-(2,6-difluorophenyl)quinazolin-8-amine, N-(4-((3R,5S)-3-amino-5-methyl-piperidin-1-yl)pyridin-3-yl)-2-(2,6-difluorophenyl)quinazolin-8-amine, N-(4-((3S,5R)-3-amino-5-methylpiperidin-1-yl)pyridin-3-yl)-2-(2,6-difluorophenyl)quinazolin-8-amine, (S)—N-(4-(3-aminopiperidin-1-yl)pyridin-3-yl)-2-(thiazol-2-yl)quinazolin-8-amine, (S)—N-(4-(3-aminopiperidin-1-yl)pyridin-3-yl)-2-(2,6-difluorophenyl)quinazolin-8-amine, amine and (S)—N-(4-(3-aminopiperidin-1-yl)pyridin-3-yl)-2-(2-fluorophenyl)quinazolin-8-amine.

4. A compound of claim 3 selected from the group consisting of (3R,4S)-3-amino-1-(3-(2-(2,6-difluorophenyl)quinazolin-8-ylamino)pyridin-4-yl)-piperidin-4-ol, (3R,4R)-3-amino-1-(3-(2-(2,6-difluorophenyl)quinazolin-8-ylamino)pyridin-4-yl)piperidin-4-ol, (3R,5S)-5-amino-1-(3-(2-(2,6-difluorophenyl)quinolin-8-ylamino)pyridin-4-yl)piperidin-3-ol, ((3R,5S)-5-amino-1-(3-(2-(2,6-difluorophenyl)quinolin-8-ylamino)pyridin-4-yl)piperidin-3-yl)methanol, N-(4-((3R,4R)-3-amino-4-fluoropiperidin-1-yl)pyridin-3-yl)-2-(2,6-difluorophenyl)quinazolin-8-amine, N-(4-((3S,5R)-3-amino-5-(fluoromethyl)piperidin-1-yl)pyridin-3-yl)-2-(2,6-difluorophenyl)quinazolin-8-amine, N-(4-((3R,5S)-3-amino-5-methylpiperidin-1-yl)pyridin-3-yl)-2-(2,6-difluorophenyl)quinazolin-8-amine, N-(4-((3S,5R)-3-amino-5-methylpiperidin-1-yl)pyridin-3-yl)-2-(2,6-difluorophenyl)quinazolin-8-amine, (S)—N-(4-(3-aminopiperidin-1-yl)pyridin-3-yl)-2-(thiazol-2-yl)quinazolin-8-amine, (S)—N-(4-(3-aminopiperidin-1-yl)pyridin-3-yl)-2-(2,6-difluorophenyl)quinazolin-8-amine, and (S)—N-(4-(3-aminopiperidin-1-yl)pyridin-3-yl)-2-(2-fluorophenyl)quinazolin-8-amine.

5. The compound of claim 1, wherein Y is piperidinyl, and is substituted with up to 4 substituents selected from hydrogen, amino, halo, hydroxyl, hydroxyl alkyl, methoxy, ethoxy, monofluoro methyl, difluoro methyl, and trifluoro methyl.

6. The compound of claim 1, wherein $R_1$ is phenyl optionally substituted with up to 4 substituents selected from halogen, alkyl having one to six carbon atoms, amino, hydroxyl, and cyano.

7. A pharmaceutical composition comprising an effective amount of a compound of claim 1.

8. A composition comprising the compound of claim 1 which further comprises at least one additional agent for the treatment of cancer.

9. A method for inhibiting PIM kinase activity in a cell, comprising contacting the cell with an effective amount of a compound of claim 1.

10. A method for treating a condition by modulation of Provirus Integration of Maloney Kinase (PIM Kinase) activity comprising administering to a patient in need of such treatment an effective amount of a compound of claim 1.

\* \* \* \* \*